US009149513B2

(12) United States Patent
Bartoov et al.

(10) Patent No.: US 9,149,513 B2
(45) Date of Patent: Oct. 6, 2015

(54) METHOD AND PHARMACOLOGICAL COMPOSITION FOR THE DIAGNOSIS AND TREATMENT OF MALE SUB-FERTILITY

(71) Applicants: Benjamin Bartoov, Moshav Hemed (IL); Ronen Yehuda, Kfar Saba (IL); Melamed Dobroslav, Ramat Gan (IL)

(72) Inventors: Benjamin Bartoov, Moshav Hemed (IL); Ronen Yehuda, Kfar Saba (IL); Melamed Dobroslav, Ramat Gan (IL)

(73) Assignee: PERINESS LTD., Givat Shmel (IL)

( * ) Notice: Subject to any disclaimer, the term of this patent is extended or adjusted under 35 U.S.C. 154(b) by 0 days.

(21) Appl. No.: 13/722,214

(22) Filed: Dec. 20, 2012

(65) Prior Publication Data
US 2013/0121985 A1 May 16, 2013

Related U.S. Application Data

(62) Division of application No. 12/311,850, filed as application No. PCT/IL2007/001250 on Oct. 18, 2007, now abandoned.

(60) Provisional application No. 60/852,402, filed on Oct. 18, 2006.

(51) Int. Cl.
A61K 38/00 (2006.01)
A61K 38/46 (2006.01)
A61K 31/00 (2006.01)
A61K 31/194 (2006.01)
G01N 33/68 (2006.01)
A61K 38/14 (2006.01)
A61K 38/17 (2006.01)

(52) U.S. Cl.
CPC ............... *A61K 38/46* (2013.01); *A61K 31/00* (2013.01); *A61K 31/194* (2013.01); *A61K 38/14* (2013.01); *A61K 38/1709* (2013.01); *A61K 38/465* (2013.01); *G01N 33/689* (2013.01); *G01N 2333/922* (2013.01); *G01N 2510/00* (2013.01); *Y10T 436/143333* (2015.01)

(58) Field of Classification Search
None
See application file for complete search history.

(56) References Cited

U.S. PATENT DOCUMENTS

| 4,868,111 | A |   | 9/1989  | Bujard et al. |
|-----------|---|---|---------|---------------|
| 4,952,496 | A |   | 8/1990  | Studier et al. |
| 4,996,155 | A |   | 2/1991  | Sick et al. |
| 5,279,823 | A |   | 1/1994  | Frenz et al. |
| 5,484,589 | A | * | 1/1996  | Salganik ................ 424/94.2 |
| 5,783,433 | A |   | 7/1998  | Frenz et al. |
| 6,251,648 | B1 |  | 6/2001  | Rosen et al. |
| 6,348,343 | B2 |  | 2/2002  | Lazarus et al. |
| 6,391,607 | B1 |  | 5/2002  | Lazarus et al. |
| 6,440,412 | B1 |  | 8/2002  | Frenz et al. |
| 6,569,660 | B1 |  | 5/2003  | Rosen et al. |
| 6,585,957 | B1 |  | 7/2003  | Adjei et al. |
| 6,932,965 | B2 |  | 8/2005  | Frenz et al. |
| 7,067,298 | B2 |  | 6/2006  | Latham et al. |
| 7,118,901 | B2 |  | 10/2006 | Suppmann et al. |
| 7,297,526 | B2 |  | 11/2007 | Shak |
| 2001/0008764 | A1 | | 7/2001 | Ax et al. |
| 2001/0044937 | A1 | | 11/2001 | Schatten et al. |
| 2003/0221206 | A1 | | 11/2003 | Schatten et al. |
| 2005/0120397 | A1 | | 6/2005 | Steller et al. |
| 2007/0259367 | A1 | * | 11/2007 | Ax et al. ..................... 435/6 |
| 2009/0053200 | A1 | * | 2/2009 | Genkin et al. ............ 424/130.1 |

FOREIGN PATENT DOCUMENTS

| CN | 1440298 A       |   | 9/2003 |
|----|-----------------|---|--------|
| CN | 1518543 A       |   | 8/2004 |
| DE | 4024530 A1      | * | 2/1992 |
| EP | 1 431 762 A1    |   | 6/2004 |
| WO | 90/07572 A1     |   | 7/1990 |
| WO | 93/25670 A1     |   | 12/1993 |
| WO | 02/03974 A2     |   | 1/2002 |
| WO | WO 02/06444     | * | 1/2002 |
| WO | WO 03/068254    | * | 8/2003 |
| WO | WO 2006/130034  | * | 7/2006 |
| WO | WO 2007/131108  | * | 11/2007 |

OTHER PUBLICATIONS

Alghamdi et al, Seminal DNase Frees Spermatozoa Entangled in Neutrophil Extracellular Traps, Biology of Reproduction 73, 1174-1181, 2005.*
Kotronias et al, Detection of herpes simplex virus DNA in human spermatozoa by in situ hybridization technique, In Vivo. Jul.-Aug. 1998;12(4):391-4.*
Gurunath et al, Defining infertility—a systematic review of prevalence studies, Human Reproduction Update, vol. 17, No. 5 pp. 575-588, 2011.*
El-Amin et al, Sero-Prevalence of Herpes Virus Infection in Sudanese Pregnant Women, Trop Med Surg 2013, 1:5.*
Isidori, et al., "Treatment of Male Infertility", Contraception, vol. 72, No. 4, pp. 314-318, (2005).
Kerin, et al., "Improved Conception Rate After Intrauterine Insemination of Washed Spermatozoa from Men with Poor Quality Semen", The Lancet, vol. 1, pp. 533-534, (1984).
Ombelet, et al., "Intrauterine insemination: a first-step procedure in the algorithm of male subfertility treatment", Human Reproduction, vol. 10, Supplement 1, pp. 90-102, (1995).

(Continued)

*Primary Examiner* — Karlheinz R Skowronek
*Assistant Examiner* — Sergio Coffa
(74) *Attorney, Agent, or Firm* — Vorys, Sater, Seymour and Pease LLP; Ari G. Zytcer

(57) ABSTRACT

Methods for treating male sub-fertility by administering a pharmaceutical composition to a subject in need thereof are provided. The pharmaceutical compositions include an agent that causes a reduction in an effect of extracellular DNA on sperm cells. The agent may be, for example, an enzyme that degrades DNA such as DNase, a substance that blocks the interaction between cell free DNA and sperm cell surface receptors, a substance that binds to DNA, a substance that inhibits endogenous sperm cell DNase, a substance that inhibits a member of a signal transduction pathway mediated by DNA binding to sperm cell surface receptors, or an agent that stimulates production of an endogenous substance that causes a reduction in an antifertility effect of cell free DNA on sperm cells.

8 Claims, 20 Drawing Sheets

(56) References Cited

OTHER PUBLICATIONS

Hinting, et al., "Possibilities and limitations of techniques of assisted reproduction for the treatment of male infertility", Human Reproduction, vol. 5, No. 5, pp. 544-548, (1990).
Comhaire, et al., "The effective cumulative pregnancy rate of different modes of treatment of male infertility", Andrologia, vol. 27, pp. 217-221, (1995).
Palermo, et al., "Intracytoplasmic sperm injection: a novel treatment for all forms of male factor infertility", Fertility and Sterility, vol. 53, No. 6, pp. 1231-1240, (1995).
Bartoov, et al., "Selection of Spermatozoa with Normal Nuclei to Improve the Pregnancy Rate with Intracytoplasmic Sperm Injection", N Engl J Med, vol. 345, No. 14, p. 1067-1068, (2001).
Bartoov, et al., "Pregnancy rates are higher with intracytoplasmic morphologically selected sperm injection than with conventional intracytoplasmic injection", Fertility and Sterility, vol. 80, No. 6, pp. 1413-1419, (2003).
Berkovitz, et al., "How to improve IVF-ICSI outcome by sperm selection", Reproductive BioMedicine Online, vol. 12, No. 5, pp. 634-638, (2006).
Who laboratory manual for the examination of human semen and sperm-cervical mucas interaction. pp. 43-44. Fourth edition 1999. World Health Organization. Cambridge University Press.
Aitken, "Sperm function tests and fertility", International Journal of Andrology, vol. 29, No. 1, pp. 69-75, (2006).
Bartoov, et al., "Real-Time Fine Morphology of Motile Human Sperm Cells is Associated With IVF-ICSI Outcome", Journal of Andrology, vol. 23, No. 1, pp. 1-8, (2002).
Shak, et al., "Recombinant human DNase I reduces the viscosity of cystic fibrosis sputum", Proc. Natl. Acad. Sci. USA, vol. 87, pp. 9188-9192, (1990).
Messing, et al., "Filamentous coliphage M13 as a cloning vehicle: Insertion of a Hindil fragment of the 1ac regulatory region in M13 replicative form in vitro", Proc. Natl. Acad. Sci. USA, vol. 74, No. 9, pp. 3642-3646, (1977).
Norrander, et al., "Construction of improved M13 vectors using oligodeoxynucleotide-directed mutagenesis", Gene, vol. 26, pp. 101-106, (1983).
Yanisch-Perron, et al., "Improved M13 phage cloning vectors and host strains: nucleotide sequences of the M13mp18 and pUC19 vectors", Gene, vol. 33, pp. 103-119, (1985).
Clos, et al., "pJC20 and pJC40—Two High-Copy-Number Vectors for T7 RNA Polymerase-Dependent Expression of Recombinant Genes in *Escherichia coli*", Protein Expression and Purification, vol. 5, pp. 133-137, (1994).
Cheng, et al., "Construction and use of λ PL promoter vectors for direct cloning and high level expression of PCR amplified DNA coding sequences", Nucleic Acids Research, vol. 20, No. 17, pp. 4591-4598, (1992).
Diederich, et al., "A Versatile Plasmid Vector System for the Regulated Expression of Genes in *Escherichia coli*", BioTechniques, vol. 16, No. 5, pp. 916-920, (1994).
Agarwal, et al., "Oxidative stress, DNA damage and apoptosis in male infertility: a clinical approach", BJU International, vol. 95, No. 4, pp. 503-507, (2005).
Alghamdi, et al., "Seminal DNase Frees Spermatozoa Entangled in Neutrophil Extracellular Traps", Biology of Reproduction, vol. 73, No. 6, pp. 1174-1181, (2005).

Bujard, et al., "A T5 Promoter-Based Transcription-Translation System for the Analysis of Proteins in Vitro and in Vivo", Methods in Enzymology, vol. 155, pp. 416-433, (1987).
The European Search Report for European Application No. 11 18 3174, completed on Dec. 28, 2011, three pages.
The European Search Report for European Application No. 11 18 3184, completed on Dec. 29, 2011, four pages.
Greco, et al., "Reduction of the Incidence of Sperm DNA Fragmentation by Oral Antioxidant Treatment", Journal of Andrology, vol. 26, No. 3, pp. 349-353, (2005).
The International Search Report for International Application No. PCT/IL2007/001250, mailed on Jul. 15, 2008, six pages.
Lavitrano, et al., "The Interaction of Sperm Cells with Exogenous DNA: A Role of CD4 and Major Histocompatibility Complex Class II Molecules", Experimental Cell Research, vol. 233, No. 1, pp. 56-62, (1997).
Lewis, et al., "DNA damage to spermatozoa has impacts on fertilization and pregnancy", Cell Tissue Res, vol. 322, No. 1, pp. 33-41, (2005).
Marchetti, et al., "Staining of human sperm with fluorochrome-labeled inhibitor of caspases to detect activated caspases: correlation with apoptosis and sperm parameters", Human Reproduction, vol. 19, No. 5, pp. 1127-1134, (2004).
McCauley, et al., "Purification and Characterization of Fertility-Associated Antigen (FAA) in Bovine Seminal Fluid", Molecular Reproduction and Development, vol. 54, pp. 145-153, (1999).
McVicar, et al., "Incidence of Fas positivity and deoxyribonucleic acid double-stranded breaks in human ejaculated sperm", Fertility and Sterility, vol. 81, Supplemental 1, pp. 767-774, (2004).
Nair, et al., "Diethylstilbestrol Induces Rat Spermatogenic Cell Apoptosis in Vivo through Increased Expression of Spermatogenic Cell Fas/FasL System", The Journal of Biological Chemistry, vol. 278, No. 8, pp. 6470-6481, (2003).
Paasch, et al., "Cryopreservation and Thawing Is Associated with Varying Extent of Activation of Apoptotic Machinery in Subsets of Ejaculated Human Spermatozoa", Biology of Reproduction, vol. 71, No. 6, pp. 1828-1837, (2004).
Said, et al., "Selection of Nonapoptotic Spermatozoa As a New Tool for Enhancing Assisted Reproduction Outcomes: An In Vitro Model", Biology of Reproduction, vol. 74, No. 3, pp. 530-537, (2006).
Sakkas, et al., "Nature of DNA Damage in Ejaculated Human Spermatozoa and the Possible Involvement of Apoptosis", Biology of Reproduction, vol. 66, No. 4, pp. 1061-1067, (2002).
Cayli, et al., "Cellular maturity and apoptosis in human sperm: creatine kinase, caspase-3 and Bcl-XL levels in mature and diminished maturity sperm", Molecular Human Reproduction, vol. 10, No. 5, pp. 365-372, (2004).
Spadafora, "Sperm cells and foreign DNA: a controversial relation", Bioessays, vol. 20, No. 11, pp. 955-964, (1998).
Takeshita, et al., "Detection of Deoxyribonucleases I and II (DNASES I and II) Activities in Reproductive Organs of Male Rabbits", Int. J. Biochem., vol. 26, No. 8, pp. 1025-1031, (1994).
Yasuda, et al., "Human seminal deoxyribonuclease I (DNase I): purification, enzymological and immunological characterization and origin", Clinica Chimica Acta, vol. 218, pp. 5-16, (1993).
Boomsma, et al., "Semen preparation techniques for intrauterine insemination", Cochrane Database Syst Rev, 2004; (3):CD004507. (Sperm selection).

\* cited by examiner

P < 0.005, n=7

*P =0.040
Using unpaired t test

*P =0.032
Using paired t test

*P <0.001, n=9

*P <0.05, n=9

*P <0.05, n=9
**P <0.005, n=9

*P <0.05, n=9

*P <0.05, n=9
*P >0.005, n=9

# P < 0.001 compared to unsorted sperm cells
** P < 0.001 compared to Fas+ sperm cells
* P < 0.001 compared to control sperm cells

METHOD AND PHARMACOLOGICAL COMPOSITION FOR THE DIAGNOSIS AND TREATMENT OF MALE SUB-FERTILITY

This is a Divisional Application filed under 35 U.S.C. §120 as a division of U.S. patent application Ser. No. 12/311,850, filed on May 20, 2009, which is a National Phase Application filed under 35 U.S.C. §371 as a national stage of PCT/IL2007/001250, filed on Oct. 18, 2007, which is an application claiming the benefit under 35 U.S.C. §119(e) of U.S. Provisional Application No. 60/852,402, filed on Oct. 18, 2006, the content of each of which is hereby incorporated by reference in their entirety.

FIELD OF THE INVENTION

The invention relates to methods and pharmacological compositions, and more specifically to such methods and pharmacological compositions for use in diagnosing and treating male sub-fertility.

LIST OF PRIOR ART

The following is a list of prior art references which are considered to be pertinent for understanding the invention. Acknowledgement of these references herein will at times be made by indicating their number from the list below within parentheses.
1. Isidori A, Latini M, Romanelli F. (1) Isidori A, Latini M, Romanelli F. Treatment of male infertility. Contraception. 2005 October; 72(4):314-8.
2. Kerin J F P, Peek J, Warms G M, Kirby C, Jeffrey R, Matthews C D, Cox L W (1984) Improved conception rate after intrauterine insemination of washed spermatozoa from men with poor quality semen. Lancet 1:533-534.
3. Ombelet W, Puttemans P, Bosmans E (1995) Intrauterine insemination: a first step procedure in the algorithm of male subfertility treatment. Hum Reprod 10:90-102.
4. Hinting A, Comhaire F, Vermeulen L, Dhont M, Vermeulen A, Vandekerckhove D (1990) Possibilities and limitations of techniques of assisted reproduction for the treatment of male infertility. Hum Reprod 5:544-548.
5. Comhaire F, Milingos S, Liapi A, Gordts S, Campo R, Depypere H, Dhont M, Schoonjans F (1995) The effective cumulative pregnancy rate of different modes of treatment of male infertility. Andrologia 27:217-221.
6. Palermo G D, Cohen J, Alikani M, Adler A, Rozenwaks Z (1995) Intracytoplasmic sperm injection: a novel treatment for all forms of male factor infertility. Feral Steril 63:1231-1240.
7. Bartoov B, Berkovitz A, Eltes F. Selection of spermatozoa with normal nuclei to improve the pregnancy rate with intracytoplasmic sperm injection. N Engl J Med. 2001 Oct. 4; 345(14):1067-8.
8. Bartoov B, Berkovitz A, Eltes F, Kogosovsky A, Yagoda A, Lederman H, Artzi S, Gross M, Barak Y. Pregnancy rates are higher with intracytoplasmic morphologically selected sperm injection than with conventional intracytoplasmic injection. Fertil Steril. 2003 December; 80(6):1413-9.
9. Berkovitz A, Eltes F, Lederman H, Peer S, Ellenbogen A, Feldberg B, Bartoov B. How to improve IVF-ICSI outcome by sperm selection. Reprod Biomed Online. 2006 May; 12(5):634-8.
10. WHO laboratory manual for the examination of human semen and sperm-cervical mucus interaction. Fourth edition 1999. World Health Organization. Cambridge university press.
11. Aitken R J. Sperm function tests and fertility. Int J Androl. 2006 February; 29(1):69-75; discussion 105-8.
12. Bartoov B, Berkovitz A, Eltes F, Kogosowski A, Menezo Y, Barak Y. Real-time fine morphology of motile human sperm cells is associated with IVF-ICSI outcome. J. Androl. 2002 January-February; 23 (1):1-8.
13. Spadafora C. Sperm cells and foreign DNA: a controversial relation. Bioessays. 1998 November; 20(11):955-64.
14. Shak S, Capon D J, Hellmiss R, Marsters S A, Baker C L. Recombinant human DNase I reduces the viscosity of cystic fibrosis sputum. Proc Natl Acad Sci USA 1990; 87: 9188-92.

BACKGROUND OF THE INVENTION

Today, in the western world about one couple out of five is sub-fertile. Sub-fertility is defined as a failure to conceive after 1 year of unprotected sexual intercourse. In about half of all sub-fertile couples, male sub-fertility is observed, and in almost 40% of such couples the sub-fertility is solely due to male factors.

Male fertility status is evaluated by a semen analysis. The most common analysis, known as "routine semen analysis", provides information on the number of spermatozoa present in the ejaculate, the proportion of motile (and/or progressively motile) sperm cells and the percentage of cells that are morphologically normal. Male sub-fertility is usually associated with one or more of low sperm production (oligozoospermia), poor sperm motility (asthenozoospermia) and abnormal sperm morphology (teratozoospermia). The combination of all three of these defects ("oligoasthenoteratozoospermia", OTA) is the most common cause of male sub-fertility. The probability of conception increases with increased sperm concentration, motility and normal morphology. The World Health Organization (WHO) has proposed guidelines specifying threshold values for these parameters for classifying semen samples as normal or abnormal (10).

Routine semen analysis, however, has many limitations resulting in a significant proportion of patients exhibiting unexplained sub-fertility. To refine the diagnosis, additional tests have been developed that provide more information on the fertilization potential of human semen. These tests include various sperm cell functional tests (11), functional morphology tests as the "motile sperm organelle morphology examination" (MSOME, 12) and tests examining the extent of DNA damage in sperm cells, for example, the sperm chromatin structure assay (SCSA, 11).

In some cases, the cause of male sub-fertility is known. These include varicocele, hormonal disorders, infections, immunological infertility, obstructions of the male genital tract and cryptorchidism. Current medical and surgical therapies are available for these conditions (1). However in a large number of cases of male sub-fertility, the cause is not known. In these cases, various treatments may be applied to sub-fertile men, often on an ad hoc basis. These treatments include antiestrogens, aromatase inhibitors, androgens, FSH, pentoxyphylline, arginine, carnitine, glutathione, vitamins (A, C and E), and oligominerals (zinc, selenium) (1).

When a treatment of male infertility does not lead to a pregnancy after a reasonable period of time or if the diagnostic measures show that no improvement in fertility status is possible, then assisted reproduction techniques (ART) may be considered. The various assisted reproduction procedures enhance the sperm fertilization potential by bypassing some or all migration barriers of the lower and upper female genital tract as well as the ovum investments. ART procedures that are common today include intrauterine insemination (IUI, 2, 3), classic in vitro fertilization (IVF, 4, 5) and IVF-Intracytoplasmic sperm injection (IVF-ICSI, 6). An improvement in ICSI is a technique known as "intracytoplasmic morphologically selected injection" (IMSI, 7-9) in which the fine morphology of motile spermatozoa is examined by high power microscopy and the spermatozoa exhibiting the best morphology of the nuclei are selected for ICSI.

Sperm cells from a variety of species have been shown In vitro to bind and take up exogenous DNA (13). DNA binding is mediated at least in part by CD4 and MHCII molecules present on the surface of sperm cells and is antagonized by the glycoprotein IF-1, present in the seminal fluid. Sperm interaction with extracellular cell free DNA activates intracellular nucleases such as DNase that cleave the sperm genomic DNA, eventually leading to a cell death process which resembles apoptosis.

Bovine DNase I has been used clinically since 1965. It is used in the former Soviet countries to treat infections caused by DNA viruses such as Herpes and adenovirus. It is believed that DNase degrades the viral DNA to mono and oligo nucleotides. This medication is usually used to treat Herpes simplex type 2 (genital herpes) infections, Herpetic eye infections caused by Herpes simplex, Herpes zoster infections, inflammation of the respiratory track as bronchitis and pneumonia and tuberculosis. For these applications it is administered either by intramuscular injections, inhalation or as eye drops. Recombinant human DNase I is another clinically used DNase I. It is an FDA approved medicine administrated by inhalation to treat cystic fibrosis (CF) patients. In these patients retention of viscous purulent secretions in the airways contributes both to reduced pulmonary function and to exacerbation of infections. Purulent pulmonary secretions contain very high concentrations of extracellular DNA released by degenerating leukocytes that accumulate in response to infection. DNase I hydrolyzes the DNA in sputum of CF patients and reduces sputum viscoelasticity (14).

SUMMARY OF THE INVENTION

The present invention is based on the novel and unexpected finding that high levels of cell-free deoxyoligonucleotide present in men's blood circulation is associated with sub-fertility and that administration of exogenous cell free DNA reduces sperm quality and causes sub-fertility. The inventors have thus found that providing sub-fertile males with a DNase may improve semen quality and fertility potential.

In accordance with a first aspect of the invention there is provided a pharmaceutical composition for treating male sub-fertility. The pharmaceutical composition of the invention comprises either an agent that blocks the effect of cell free deoxyribonucleic acid molecules on sperm cells or an agent that induces production of an endogenous substance that blocks the effect of cell free deoxyribonucleic acid molecules on sperm cells. For instance the pancreas and parotid glands can be stimulated to secrete elevated levels of DNase. Stimulation of pancreatic and parotid acinar cells can be exerted using either inositol 1,4,5-trisphosphate ($InsP_3$) that activates $InsP_3$ receptor or by $Ca^{2+}$ that activates ryanodine receptors. Activation of these two receptors causes $Ca^{2+}$ release into acinar cells, initiating secretion from these organs. The pharmaceutical composition of the invention will further include a pharmaceutically acceptable carrier.

In accordance with a second aspect of the invention, there is provided a method for treating a male, the method comprising administering to the male either an agent that blocks the effect of cell free deoxyribonucleic acid molecules on sperm cells or an agent that induces production of an endogenous substance that blocks the effect of cell free deoxyribonucleic acid molecules on sperm cells.

According to a preferred embodiment, the agent is a protein, preferably an enzyme which affects the level of cell free deoxyribonucleic acid molecules in body fluids. According to this embodiment, the enzyme is preferably a deoxyribonuclease (DNase). The DNase may be an endodeoxyribonuclease or an exodeoxyribonuclease (endodeoxyribonuclease cleaves inside the molecules while exodeoxyribonuclease cleaves from one end of the molecule, either 3' or 5').

A wide variety of DNases are known, which differ in their substrate specificities, chemical mechanisms, and biological functions. Non-limiting DNases which are applicable in accordance with the invention are DNase I, DNase II, DNase gamma, caspase-activated DNase (CAD), L-DNase II, DHPII. In accordance with a preferred embodiment of the invention, the DNase is DNase I. The DNase may be of animal, plant, bacteria, virus, yeast or protozoan origin, or may be a recombinant DNase, preferably a human recombinant DNase.

In accordance with another embodiment of the invention, the agent may be a molecule that interferes with the ability of deoxyribonucleic acid molecule to bind to receptors at the surface of sperm cells. These molecules may be molecules that bind and block the receptors or molecules that bind and block deoxyribonucleic acid molecules. Molecules that block the receptor may be of low molecular weight, for example deoxyribonucleotides dimmers, phosphodeoxyribosyl pyrophosphate (PdRPP), deoxyribonucleotides or metal ion or high molecular weight such as peptides, polypeptides, proteins, antibodies or glycoproteins. In a preferred embodiment, the molecule is glycoprotein IF-1 or an analog thereof capable of blocking the interaction of cell free DNA with sperm cell receptors. Molecules that bind and block deoxyribonucleic acid molecules may be peptides, polypeptides, proteins, DNA binding proteins, nuclear proteins (as histons, protamines) or antibodies. Deoxyribonucleic acid molecules may also exert a deleterious effect on sperm cells by binding at the surface of sperm cell proteins and lipids that are not receptors. In this case the agent may be a molecule that interferes with this binding.

In accordance with another embodiment of the invention, the agent may be a molecule that blocks a stage in a signal transduction pathway generated by binding of deoxyribonucleic acid molecule to receptors at the surface of sperm cells. The agent may be a low molecular weight compound or a polymer for example caspase inhibitors such as ZVAD and bcl-2 protein family or caspase dominant negative proteins.

Sperm cell damage caused by cell free DNA may involve elevated DNase activity inside the sperm cells. Thus, in accordance with another embodiment of the invention, the pharmaceutical composition of the invention may comprise a DNase inhibitor that inhibits endogenous DNase activity within the sperm cells. The agent may be a low molecular weight compound or a polymer. Preferred agents include aurintricarboxylic acid (ATA), citrate or a functional analog thereof.

The composition may include in combination with the agent pharmaceutically acceptable carriers. By the term "pharmaceutically acceptable carrier" it is meant any one of inert, non-toxic, excipients, which essentially do not react with the agent that interferes with DNA having an effect on sperm cells and is added thereto in order to give form or consistency to the composition and to provide protection from degradation of the agent and increase its survival outside and inside the body and to obtain penetration into the body and delivery into the body fluids and to facilitates distribution of the agent in the subject's body and delivery to the target site (either to the cell free DNA, to the target cell surface receptor or to get into the sperm cell).

In accordance with one embodiment, the composition is in a form suitable for oral administration. In accordance with another embodiment, the composition is in a form suitable for injection, preferably, intramuscular (IM), subcutaneous or intravenous (i.v.) injections. In accordance with yet another embodiment, the composition is in the form suitable for inhalation. While other forms of administration are also applicable, it is noted that oral administration is a preferred route in accordance with the invention due to a better compliance to the treatment.

Semen samples obtained from males treated by the method of the invention may be used in any conventional assisted reproduction technique (ART). A non-limiting list of assisted reproduction techniques include intra uterine insemination (MI), in vitro fertilization (classical IVF), intra-cytoplasmic sperm injection (ICSI) and intra-cytoplasmatic morphologically-selected injection (IMSI) as well as other techniques as known in the art of fertility.

The agent in accordance with the invention is administered and dosed in accordance with good medical practice, taking into account the clinical condition of the male subject, the site and method of administration, scheduling of administration, subject's age, body weight and other factors known to medical practitioners. The doses may be single doses or multiple doses over a single day or over a period of several days/weeks/months (etc.). The treatment generally has a length proportional to the severity of the sub-fertility condition, agent's effectiveness and the male subject being treated.

The dosage can be readily determined by administering to a plurality of tested subjects (subjects exhibiting sub-fertility) various amounts of the tested agent and then plotting the change in semen quality as a function of the dosage. Alternatively, the dosage may be determined through experiments performed in appropriate animal models and then extrapolating to human beings using one of a plurality of conversion methods. As known, the amount which is considered to be effective in a subject may depend on a variety of factors such as the mode of administration (for example, oral administration may require a higher dose to achieve a given plasma level of the agent than an intravenous administration); the age, weight, body surface area, health condition and genetic factors of the subject; as well as drugs being simultaneously administered to the subject.

The duration of treatment should be determined according to the semen quantity and quality. Spermatogenesis occurs within the testes and takes approximately 64 days in humans. It is followed by 8-10 days of epididymal transport (EPT). The deleterious effect of cell free DNA is observed in different sections of the male genital track: the seminiferous tubules of the testes and the cauda epididymis. Thus cell free DNA can affect different stages of spermatogenesis, producing damage to sperm cells manifested at different levels of severity. Testes damage is both quantitative and qualitative while epididymal damage is mainly qualitative. Thus the duration of the treatment can vary and should be determined according to the semen quantity and quality. The treatment duration is preferably selected from the following regimes:

Acute Treatment:
A. 10 days—This course is aimed at reducing the effect of cell free DNA on sperm cells during epididymal transport.
B. 16 days—This course is aimed at reducing the effect of cell free DNA on sperm cells during the maturation phase of the spermiogenesis and during the epididymal transport.

Semi-Chronic Treatments:
C. 26 days—This course is aimed at reducing the effect of cell free DNA on sperm cells during one spermatogenic cycle and during the epididymal transport.
D. 32 days—This course is aimed at reducing the deleterious effect of cell free DNA on sperm cells during full spermiogenesis and during epididymal transport.

Chronic Treatments:
E. 74 days—This course is aimed at reducing the deleterious effect of cell free DNA on sperm cells during full spermatogenesis and during epididymal transport.

The invention also provides methods for evaluating male fertility potential. In accordance with this aspect of the invention, the level of cell-free deoxyribonucleic acid molecules and/or an agent that inhibits the effect of cell-free deoxyribonucleic acid molecule on sperm cells is determined in a body fluid of a subject. When the level of the cell-free deoxyribonucleic acid molecules is statistically significantly greater than a predefined threshold and/or said amount of said agent level is statistically significantly lower than a predefined threshold, the subject is diagnosed as having sub-fertility. According to a preferred embodiment, the agent is a protein, preferably an enzyme which affects the level of cell free deoxyribonucleic acid molecules in body fluids. According to this embodiment, the enzyme is preferably a deoxyribonuclease (DNase). According to the results of the determination, an optimal assisted reproduction technique ART may be selected in order to overcome sub-fertility. The body fluid may be for example, whole blood, blood plasma, blood serum, semen, seminal plasma, lymph fluid, sweat, saliva or tears.

In accordance with another embodiment, an activity of a marker indicative of male fertility potential is determined in sperm cells. When the activity is statistically significantly greater than a predefined threshold, the subject is diagnosed as being sub-fertile. According to the results of the determination, an optimal ART may be selected in order to overcome sub-fertility. The inventors have found that intravenous injection of deoxyribonucleic acid molecules to male mammals induced activation of the apoptotic markers Fas receptor, caspas 3 and endogenous deoxyribonuclease (DNase) in their sperm cells and that elevated expression of the Fas receptor on the surface of sperm cells is indicative of sub-fertility. Thus the marker may be an apoptosis associated protein and according to this embodiment, the apoptosis associated protein is preferably the cell surface Fas receptor, the intracellular marker caspase-3 or endogenous deoxyribonuclease (DNase). Another marker is the complex DNA-DNA receptor. Fas receptor expression on sperm cells may be determined immunologically using anti Fas receptor antibodies. The antibodies can be detected either by conjugation to a florescent dye or using any method known in the art (immunohistochemistry, peroxidase, alkaline phosphatase and others).

The invention also provides a method for selecting a sub-population of sperm cells having an enhanced conception capacity for use in an assisted reproduction technique, comprising removing from a semen sample sperm cells that express a membrane marker indicative of apoptosis so as to obtain said sub-population of sperm cells. A preferred marker is the Fas receptor. Another marker is the complex DNA-DNA receptor. Preferably, the selection of sperm cells that express the marker utilizes an antibody against the marker. The sperm cells which react with the antibody are recognized as those unable to obtain durable pregnancy and are removed from the sample. The antibody may be fluorescently labeled in which case sperm cells bound to the antibodies are removed using fluorescence-activated cell sorter. The antibody may be bound to resin beads and the unbound sperm cells are separated from the resin-bound sperm cells using a column, centrifugation or magnets.

Thus, in one of its aspects, the invention provides a pharmaceutical composition for treating male sub-fertility comprising an enzyme that degrades DNA and a physiologically acceptable carrier.

In another of its aspects, the invention provides a pharmaceutical composition for treating male sub-fertility comprising a substance that blocks the interaction between cell free DNA and sperm cell surface receptors and a physiologically acceptable carrier.

In another of its aspects, the invention provides a pharmaceutical composition for treating male sub-fertility comprising a substance that binds to DNA and a physiologically acceptable carrier.

In another of its aspects, the invention provides a pharmaceutical composition for treating male sub-fertility comprising a substance that inhibits endogenous sperm cell DNase and a physiologically acceptable carrier.

In another of its aspects, the invention provides a pharmaceutical composition for treating male sub-fertility comprising a substance that inhibits a member of a signal transduction pathway mediated by DNA binding to sperm cell surface receptors and a physiologically acceptable carrier.

In another of its aspects, the invention provides a pharmaceutical composition for treating male sub-fertility comprising an agent that stimulates production of an endogenous substance that causes a reduction in an antifertility effect of cell free DNA on sperm cells and a physiologically acceptable carrier.

In another of its aspects, the invention provides a method for treating male sub-fertility comprising administering an enzyme that degrades DNA.

In another of its aspects, the invention provides a method for treating male sub-fertility comprising administering a substance that blocks the interaction between cell free DNA and sperm cell surface receptors.

In another of its aspects, the invention provides a method for treating male sub-fertility comprising administering a substance that binds DNA.

In another of its aspects, the invention provides a method for treating male sub-fertility comprising administering a substance that inhibits endogenous sperm cell DNase.

In another of its aspects, the invention provides a method for treating male sub-fertility comprising administering a substance that inhibits a member of a signal transduction pathway mediated by DNA binding to a sperm cell surface receptors.

In another of its aspects, the invention provides a method for treating male sub-fertility comprising administering an agent that stimulates production of an endogenous substance that causes a reduction in an antifertility effect of cell free DNA on sperm cells.

In another of its aspects, the invention provides a method for determining a fertility status in a male subject, comprising:
(a) obtaining from the subject a sample of a body tissue or fluid;
(b) measuring in the sample a cell-free DNA level or a level of an agent that causes a reduction in the effect of cell-free DNA on sperm cells;
(c) comparing the measured level to one or more predetermined threshold values; and
(d) determining the fertility status based upon the comparison.

In another of its aspects, the invention provides a method for determining a fertility status in a male subject, comprising:
(a) obtaining from the subject a sample containing sperm cells;
(b) measuring in the sperm cells a level of a substance indicative of apoptosis;
(c) comparing the measured level to one or more predetermined threshold values; and
(d) determining the fertility status based upon the comparison.

In another of its aspects, the invention provides a method for assisted reproduction comprising:
(a) Obtaining a sample containing sperm cells from a male treated by the method of the invention;
(b) Utilizing the sample in an assisted reproduction technique (ART).

In another of its aspects, the invention provides a method for selecting an assisted reproduction technique (ART) comprising:
(a) determining a fertility status in a male subject by the method of the invention; and
(b) determining an ART based upon the fertility status.

In another of its aspects, the invention provides a method for selecting sperm cells in a sperm cell population for use in an assisted reproduction technique, comprising
(a) obtaining a semen sample containing sperm cells; and
(b) removing from the semen sample sperm cells that express an apoptotic marker so as to obtain a sub-population of sperm cells.

In another of its aspects, the invention provides a pharmaceutical composition for treating male sub-fertility comprising an agent selected from:
(a) an agent that causes a reduction in an effect of extracellular DNA on sperm cells; and
(b) an agent that stimulates production of an endogenous substance that causes a reduction in an effect of extracellular DNA on sperm cells; together with a physiologically acceptable carrier.

In another of its aspects, the invention provides a method for treating male sub-fertility comprising administering an agent selected from:
(a) an agent that causes a reduction in an effect of extracellular DNA on sperm cells; and
(b) an agent that stimulates production of an endogenous substance that causes a reduction in an effect of extracellular DNA on sperm cells.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

EXAMPLES

Materials

Figure 1:
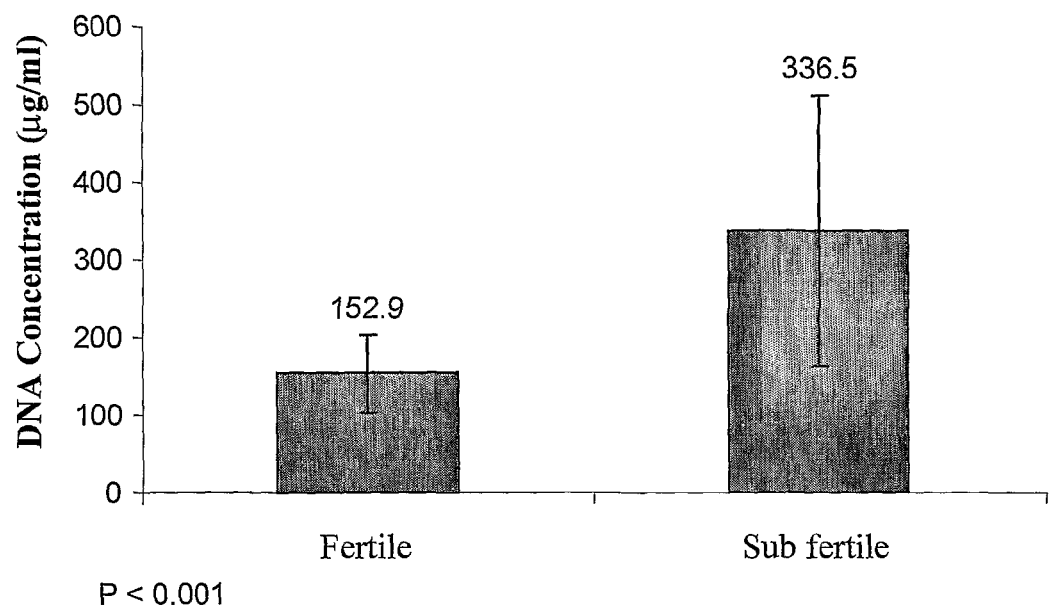
FIG. 1 is a histogram showing DNA concentration in fertile and sub fertile men.

Standard DNA Solution:
100 mM calf thymus DNA was dissolved in double distilled water (DDW).

DPA Solution:
1.5 gr of Diphenylamine was dissolved in 100 ml glacial acetic acid and 1.5 ml sulfuric acid was added. On the day of use, 0.5 ml of acetaldehyde was added.

Polyvinyl Pyrrolidone (PVP) Solution:
PVP medium 10890001 obtained from Medi-Cult.

Kunitz DNase Activity Reaction Buffer:
5 mM $MgSO_4 \times 7H_2O$, 0.1 M NaAcetate pH 5, 4 mg % Calf thymus DNA Methods DNA and Deoxyoligonucleotide Levels (Burton Method):
Standard DNA solution was diluted to 5, 10, 20 and 50 μg/ml in 166 μl. To each 166 μl of plasma samples or DNA standard sample, 166 μl of 1N $HClO_4$ and 664 μl of DPA solution were added. Samples were incubated at 37° C. for 20 h, and then centrifuged for 10 min (15,000 g, 37° C.). 300 μl of the supernatant was transferred to a 96 well plate and measured in a spectrophotometer at 600 nm.

Semen Volume, Sperm Density and Sperm Concentration:
The volume of each semen ejaculate was measured using a pipette.

Sperm concentration was determined by counting the cells using either Helber hemocytometer or Neubauer hemocytometer (Helber is used when sperm concentration is high and Neubaure when it is low).

Sperm density (=cell number in whole ejaculate) was calculated by multiplying the ejaculate volume by sperm concentration.

Sperm Motility and Progressive Motility:
Motile and non-motile sperm cells were counted using either Helber hemocytometer or Neubauer hemocytometer and the percent of motile sperm cells was calculated accordingly. A sample of 20 random motile sperm cells was examined for progressive motility by examining their ability to progress in a straight line through 200 μm and the percentage of progressively motile sperm cell was calculated accordingly.

Sperm Morphology Using the Eosin-Nigrosin Staining Technique:

Sperm cells were stained using 2% eosin, a nuclear staining and 10% nigrosin for the background. 50 sperm cells were assessed using light microscopy at a magnification of 1000× under immersion oil. The sperm morphology analysis was measured according to the WHO guidelines (10).

Dry and Wet (Regular) Motile Sperm Organelle Morphology Examination (MSOME):

Sperm Preparation for Morphological Observation in Wet (Regular) MSOME:

An aliquot of 1-2 µl of the sperm suspension containing a few thousand spermatozoa was transferred to a microdroplet of sperm medium containing 0%-8% polyvinyl pyrrolidone (PVP) solution and placed in a glass-bottom dish under paraffin oil. Morphological assessment of the sperm cells in motion was made possible by the creation of small bays extending from the rim of the droplets, which captured the heads of the motile spermatozoa.

Sperm Preparation for Morphological Observation in Dry MSOME:

Fresh ejaculate post liquefaction was transferred to 15 ml round bottom tubes at room temperature (22-25° C.). The soft pellet of ejaculated sperm cells was obtained by centrifugation in swing-out buckets at 1500 RPM for 15 minutes at room temperature. The seminal plasma supernatant was removed. The sperm pellet was suspended in 1 ml Ferticult-IVF medium (FertiPro N.V. Beernem, Belgium) and then re-centrifuged at 1500 RPM for 5 minutes at room temperature. The tubes were then transferred to a 5% $CO_2$, 37° C. incubator for a 40 minute swim-up incubation, inclined at 45°. Supernatant was than carefully removed until the interphase of the sperm pellet. The swim-up supernatant was centrifuged at 1500 RPM for 5 minutes at room temperature and the supernatant was discarded. The pellet was smeared on microscope glass slides and air dried.

Sperm MSOME Observation:

Sperm cells were examined at 21° C. by an inverted microscope (Olympus IX 70) equipped with Nomarski optics, an Uplan Apo X 100/1.35 objective lens, and a 0.55 NA condenser lens. The images were captured by a DXC-950P color video camera (Sony), which has a ½-inch, 3-chip power HAD CCD containing some 380 000 effective picture elements (pixels) for high-quality image production, and a color video monitor (Sony PVM-14M4E, HR-Trinitron). The morphological assessment was conducted on the monitor screen which, under the above configuration, reached a real magnification of 6300, One-hundred motile spermatozoa from each sperm sample were examined for the morphological state of 6 subcellular organelles: acrosome, postacrosomal lamina, neck, mitochondria, tail, and nucleus. The first 5 of these subcellular organelles were considered morphologically normal or abnormal on the basis of the presence of specific malformations, which were defined as disclosed in Bartoov et al, 1981; Glezerman and Bartoov, 1993. For the nucleus, the morphological state was defined by both shape and chromatin content. The criteria for a normally shaped nucleus by MSOME are smooth, symmetric, and oval configurations. The normal range of the length and width of the sperm nucleus was taken as 4.75±0.28 µm and 3.28±0.20 µm, respectively (average±standard deviation) while sperm cells outside of this range were considered abnormal. The nuclear chromatin mass is homogenous, with no regional nuclear disorders and containing no more than one vacuole with borderline diameters of 0.78±0.18 µm from the front view. To be considered morphologically normal, a sperm nucleus had to have both normal shape and normal chromatin content. A sperm cell exhibiting a normal nucleus as well as a normal acrosome, postacrosomal lamina, neck, tail, mitochondria, and no cytoplasmic droplet or cytoplasm around the head was classified as morphologically normal.

Sperm Chromatin Structure Assay (SCSA):

The SCSA determines the percentage of spermatozoa with abnormal chromatin structure. Abnormal chromatin structure was defined as increased susceptibility of sperm DNA to acid-induced denaturation in situ. Amounts of DNA denaturation per cell were determined by flow cytometry which measured the shift of green (native DNA) to red (denatured, single-stranded DNA) fluorescence in acridine-orange stained nuclei. This shift is expressed as the DFI (DNA Fragmentation Index), which is the ratio of red to total (red+green) fluorescence intensity, representing the amount of denatured single stranded DNA over the total cellular DNA. In the SCSA, DFI was calculated for each spermatozoon in a sample, and the results were expressed as the mean for 5000 sperm cells. Aliquots of 100 µl sperm cell suspension were mixed with 2 ml TNE buffer solution (0.01 M Tris, 0.15 M NaCl, 0.001 M EDTA, pH 7.4) and centrifuged at $400 \times g_{max}$ for 15 min at 25° C. The final pellet was resuspended in 2 ml TNE buffer. The suspension was centrifuged at $3000 \times g_{max}$ for 15 min at 4° C. The nuclei pellet obtained was fixed by forceful pipetting into a 500 µl fixation solution (acetone: 70% ethanol, $1:1^v/_v$). All steps of the above procedure were performed at 4° C. The sample was centrifuged at $3000 \times g_{max}$ for 15 min at room temperature and the pellet was mixed with 100 µl acid-detergent solution (0.08 M HCl, 0.15 M NaCl, 0.1% Triton X-100, pH 1.2) for 30 seconds at 4° C. Then, the sample was stained by adding 5 µl of acridine orange (AO) staining solution containing 6 mg/ml of AO. The sample was diluted with 500 µl Citric buffer (0.037 M Citric acid, 0.126 M $Na_2HPO_4$, 0.001 M EDTA, 0.15 M NaCl, pH 6.0). Afterward, the sample was subjected to flow cytometry on a Becton-Dickenson FACSort flow cytometer, San Francisco, Calif., USA equipped with ultrasense and a 15 mW argon ion laser with an excitation wavelength of 488 nm. The DFI ratio was calculated with a ratio-time 1.1 software package written by Jan van der Aa (Becton-Dickenson, Erembodegem, Belgium) and with WinMDI 2.8 software. The DNA Fragmentation Index (DFI) is the mean fluorescence of sperm cells with nuclear DNA fragmentation. The % DNA Fragmentation Index (% DFI) is the percentage of sperm cells with nuclear DNA fragmentation. This parameter was computed on the basis of the distribution of the DFI.

Intracellular and Blood Plasma DNase Activity:

Sperm cells were subjected to three cycles of freezing and thawing and were then centrifuged for 10 min (27,000 g, 4° C.). Plasma was separated from the blood by centrifugation in EDTA tubes 0.3 ml of the supernatant was added to 0.6 ml of DNase activity buffer and the mixture was measured in a spectrophotometer at 260 nm against a reference that contained only buffer and medium. Calibration curves were made using a commercial bovine DNase I. Sperm cell internal DNase was measured in Kunitz units. One Kunitz unit is defined as the amount of DNase that produces an increase of 1 O.D. per minute at 260 nm in a 1 cm pathlength at pH 5 at 25° C., in a reaction buffer that contains 5 mM $MgSO_4 \times 7H_2O$, 0.1 M NaAcetate pH 5 and 4 mg % Calf thymus DNA. Plasma DNase was measured in Bartoov units. One Bartoov unit (BU) is defined as the amount of enzyme that produces a $\Delta A_{260}$ of 0.001 per min in 1 cm pathlength at pH 7.5 at 25° C., in a reaction buffer that contains 0.1M Tris, 10 mM $CaCl_2$, 10 mM $MnCl_2$ and 0.05 mg/ml calf thymus DNA.

Fas Receptor Expression on Sperm Cells:

Sperm cells were washed with PBS and incubated in 4% paraformaldehyde (PFA) for 30 min at 25° C. The cells were then incubated for 15 min in blocking solution (1% BSA in PBS) and then incubated for 40 min with goat anti-Fas receptor antibodies. Anti human-Fas receptor antibody was labeled with FITC and no second antibody was needed. When mice sperm cells were used, the cells were washed with PBS and incubated for 30 min. with a second antibody—anti goat labeled with FITC. Cells were washed and florescence was measured in a Becton-Dickenson FACSort Flow Cytometer.

Caspase-3 Activity in Sperm Cells:

Caspase-3 activity was measured using a calorimetric kit obtained from R&D Company. Sperm cells were washed with PBS, incubated in lysis buffer for 10 min at 4° C. and centrifuged for 1 min at 10000 g. 50 μl reaction buffer and 5 μl of caspase 3 colorimetric substrate were added to each 50 μl of supernatant and incubated for 2 h at 37° C. Activity was measured in a spectrophotometer at 405 nm.

Separation of Fas Receptor Expressing Sperm Cells from Non-Fas Receptor Expressing Sperm Cells:

Sperm cells were washed with PBS and incubated for 30 min with goat anti-Fas receptor antibodies. Anti human-Fas receptor antibody was labeled with biotin and no second antibody was needed. When mice sperm cells were used, the cells were washed with PBS and incubated for additional 30 min. with a second antibody—anti goat labeled with FITC. The cells were then washed with PBS and incubated for 20 min with either anti-biotin antibody conjugated to micro beads containing iron ions (from Myltenyi biotech Company) for caspas activity determination, or anti-FITC antibody conjugated to these micro beads for mice insemination. Separation of Fas receptor positive and negative sperm cells were performed as follows: Cells were washed with PBS and transferred through an immuno-magnetic separation column of MACS from Myltenyi biotech Company. Unlabeled sperm cells that did not express Fas receptor flowed through the column without binding. Sperm cells that expressed Fas receptor were bound to the column and eluted latter using pistons pressure.

Examination of Plasma DNase in Mice Following Oral or Injection Administration

C57/black mice were starved for 12 h and than received either oral administration of PBS (placebo, n=10) or oral administration of 9 mg DNase I in 200 μl PBS (n=14), or intraperitoneal injection of 3 mg DNase I in 200 μl PBS (n=6). Control mice were not treated at all (n=10). Blood was collected from the heart of the mice 40 min after injection or 1 h after oral administration. Plasma was separated from the blood by centrifugation in EDTA tubes and stored at −20° C. DNase activity in the plasma was determined in Bartoov units.

Results

In Vivo Effects of Cell Free DNA

Figure 2:
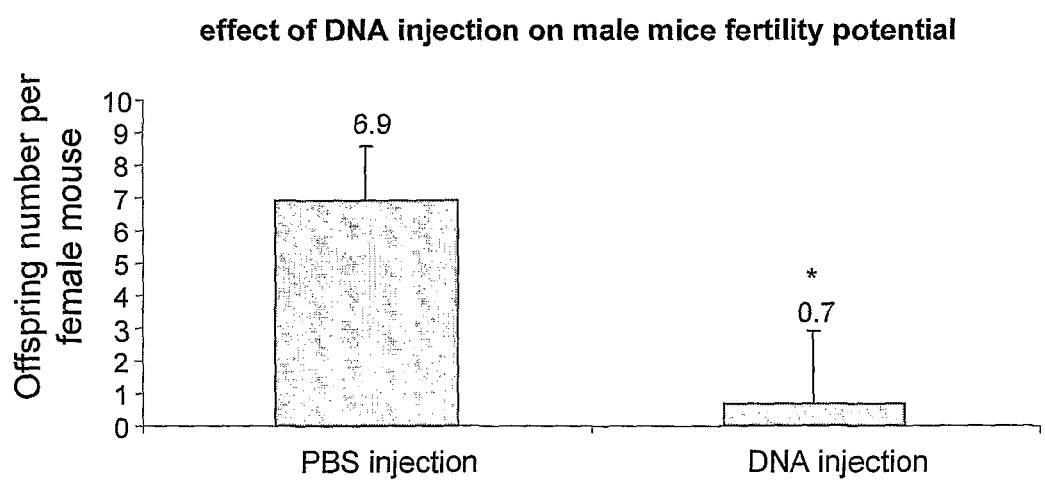
FIG. 2 shows a histogram of the effect of DNA injections on the fertility potential of male mice.
Figure 3:
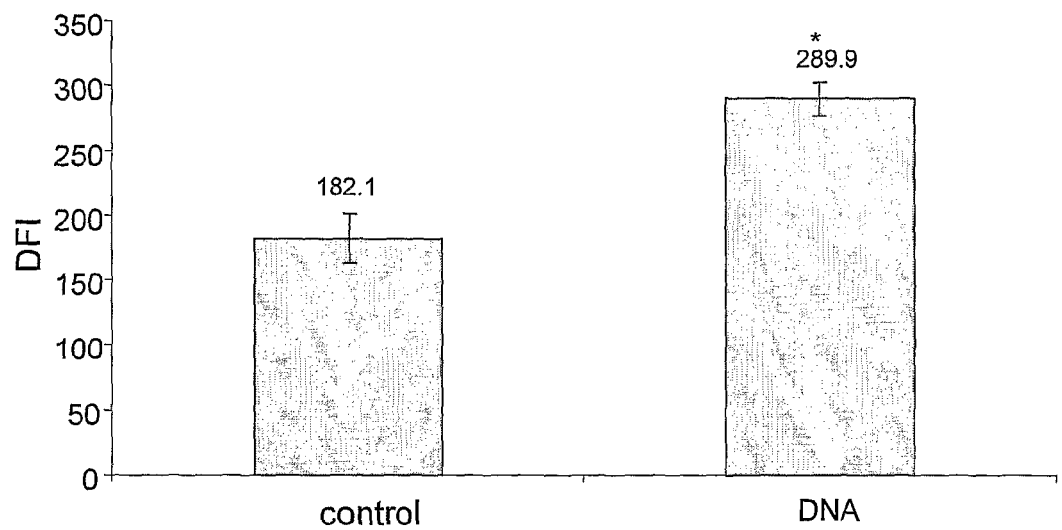
FIG. 3 is a histogram showing the effect of injection of cell free DNA to mice on sperm cell chromatin stability.
Figure 4:
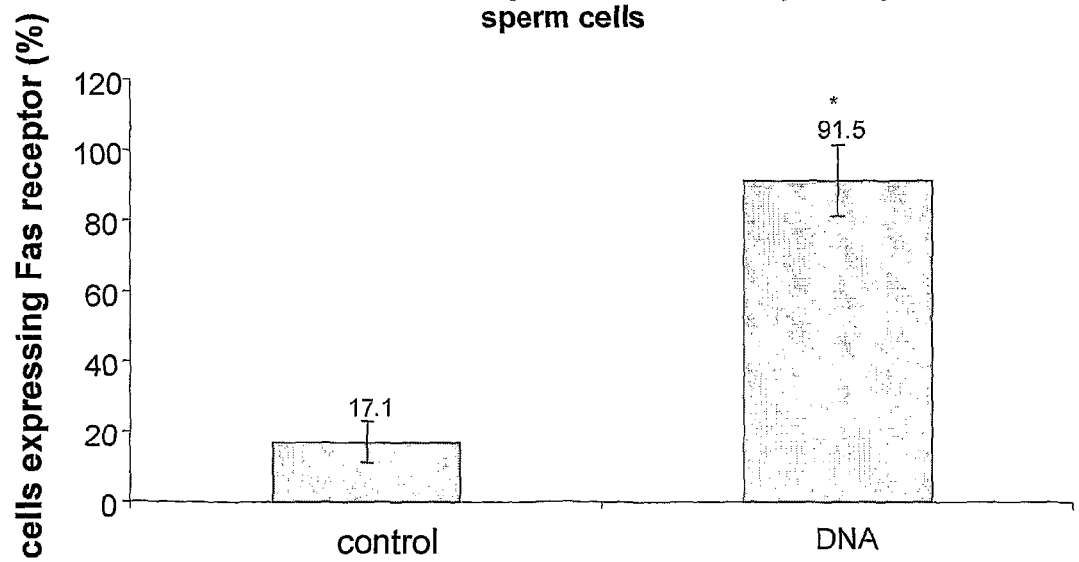
FIG. 4 is a histogram showing the effect of injection of cell free DNA to mice on the percentage of sperm cells expressing Fas receptor.
Figure 5:
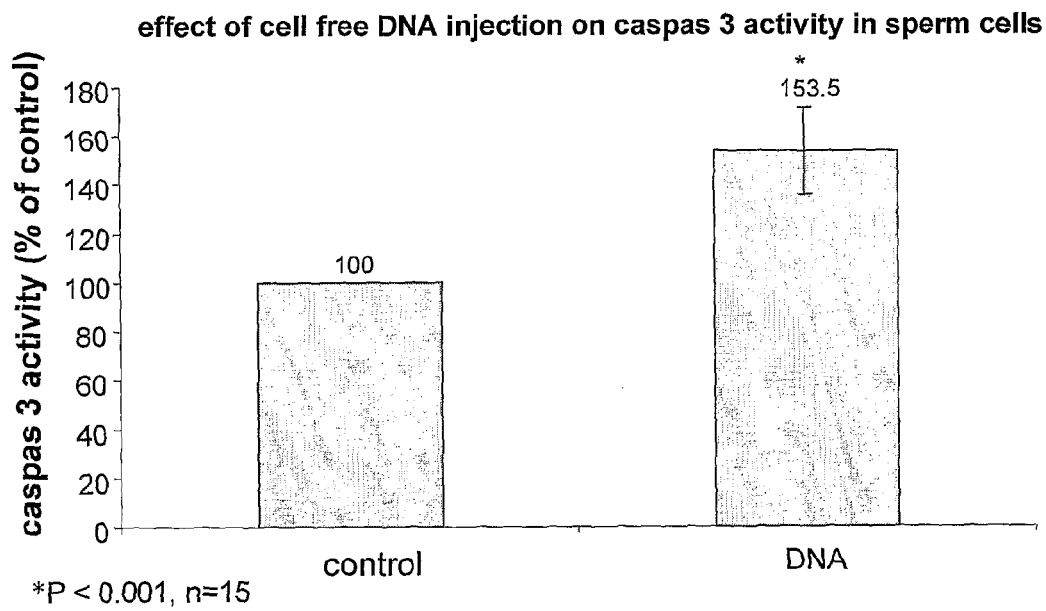
FIG. 5 is a histogram showing the effect of injection of cell free DNA to mice on caspas 3 activity in their sperm cells.
Figure 6:
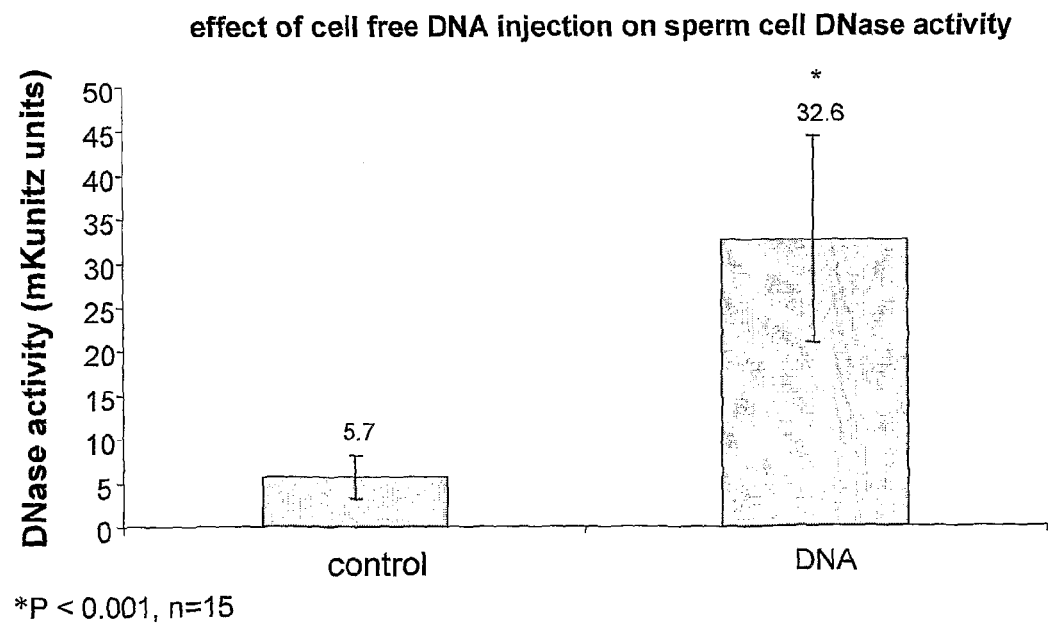
FIG. 6 is a histogram showing the effect of injection of cell free DNA to mice on endogenous DNase activity in their sperm cells.

As observed in FIG. 1, endogenous cell free DNA levels are elevated in the blood of sub-fertile men compared to fertile men, indicating a correlation between high blood DNA level and sub-fertility. Indeed intravenous injection of cell free DNA into male mice impaired their fertility potential: Two groups of 10 male mice received intravenous injections of either 200 μg cell free DNA or PBS over 15 days. The mice were then mated with female mice and the number of offspring was counted in both groups. FIG. 2 shows that mating with the control mice yielded 6.9±1.7 offspring per female while mating with the DNA injected mice yielded 0.7±2.2 offspring per female. In addition intravenous injection of cell free DNA into mice impaired their sperm cell nuclear quality, as observed by a reduction in sperm cell chromatin stability as expressed in an increase in the DFI (FIG. 3). Moreover intravenous injection of cell free DNA into mice induced activation of the apoptotic markers Fas receptor, caspas 3 and DNase within their sperm cells (FIGS. 4-6).

Figure 7:
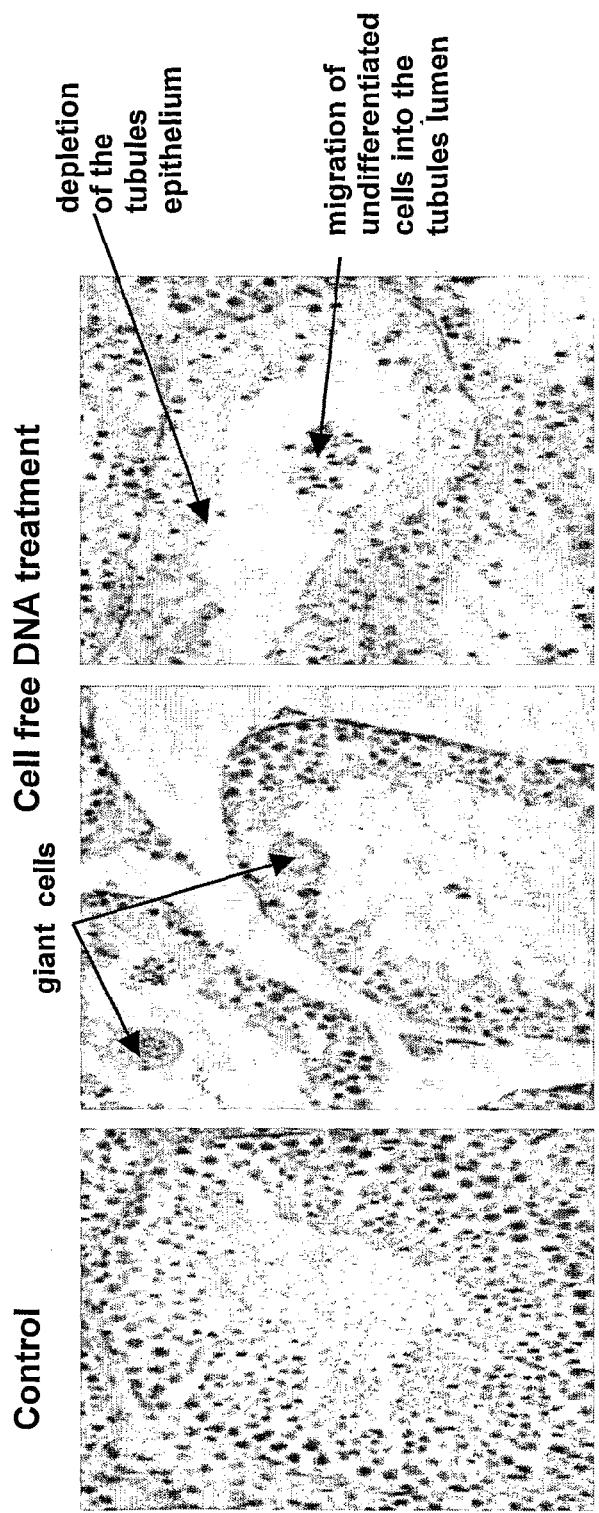
FIG. 7 shows morphological damage caused to testis tissue by DNA injection.
Figure 8:
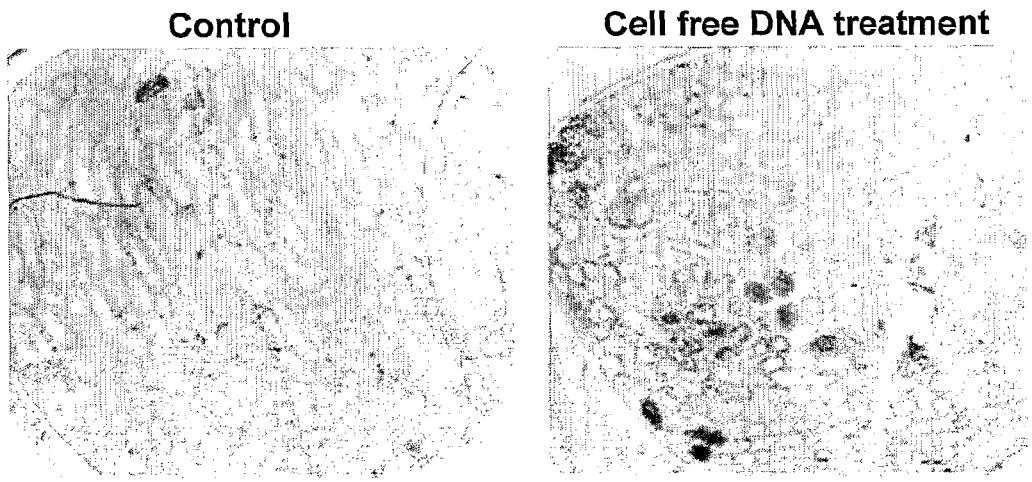
FIG. 8 shows apoptotic damage caused to testis tissue by DNA injections (TUNEL staining)
Figure 9:
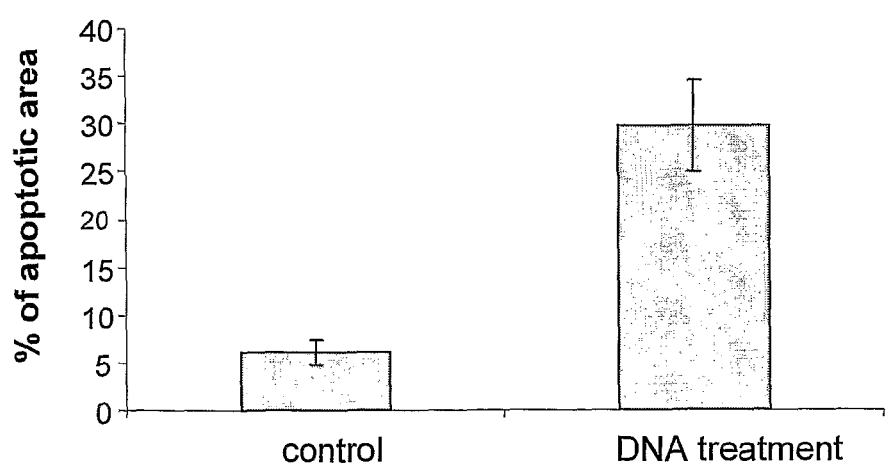
FIG. 9 shows quantification of the apoptotic damage caused to testis tissue by DNA injections.
Figure 10:
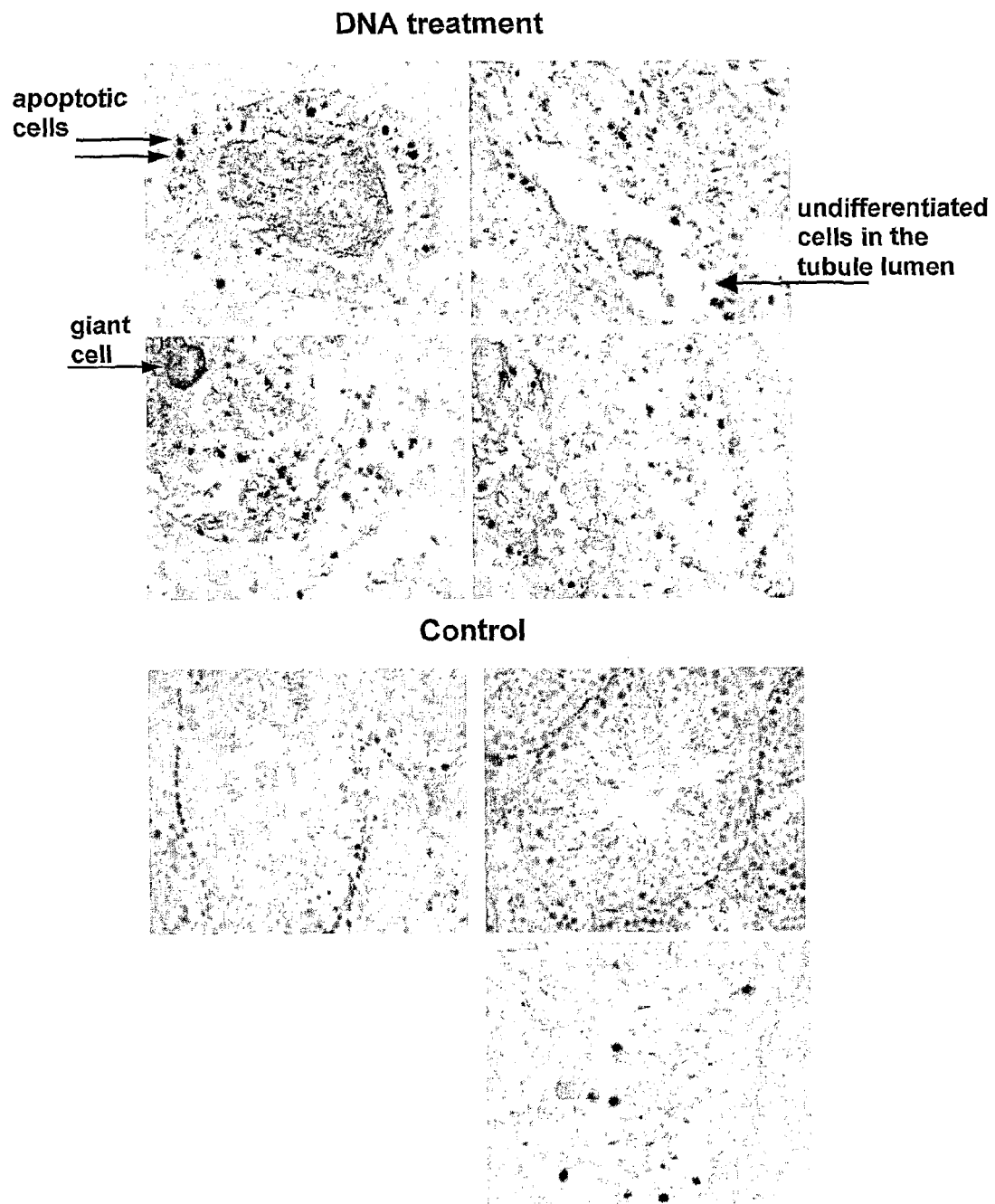
FIG. 10 shows morphological and apoptotic damage caused to testis tissue by DNA injections (TUNEL staining)

Cell free DNA injection affects not only the sperm cells but also the testis tissue. As observed in FIGS. 7 and 10, cell free DNA caused appearance of giant cells and depletion of the tubule epithelium by sloughing of testicular mature and immature germinal cells into the tubule lumen. Cell free DNA injection also caused the appearance of large apoptotic areas (FIGS. 8-10). Spermatogenesis in the testes takes approximately 64 days in humans. Thus, testes impairment caused by DNA is expected to have an impact on sperm cell development over a long period of time and repair of such damage would require prolonged treatment.

Intramuscular Administration of DNase I

Figure 11:
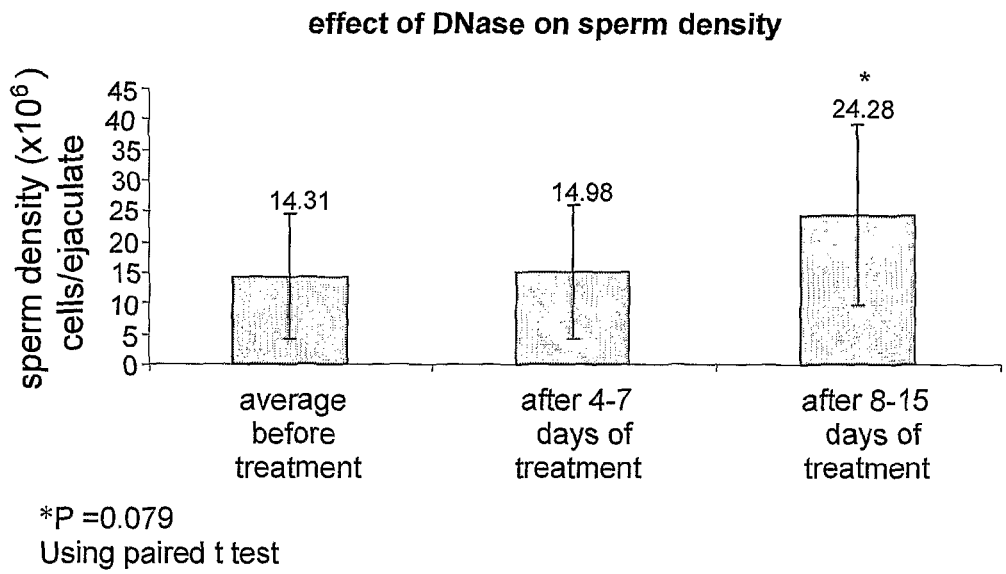
FIG. 11 is a histogram showing the effect of intramuscular DNase injections on sperm density in semen of sub-fertile men.
Figure 12:
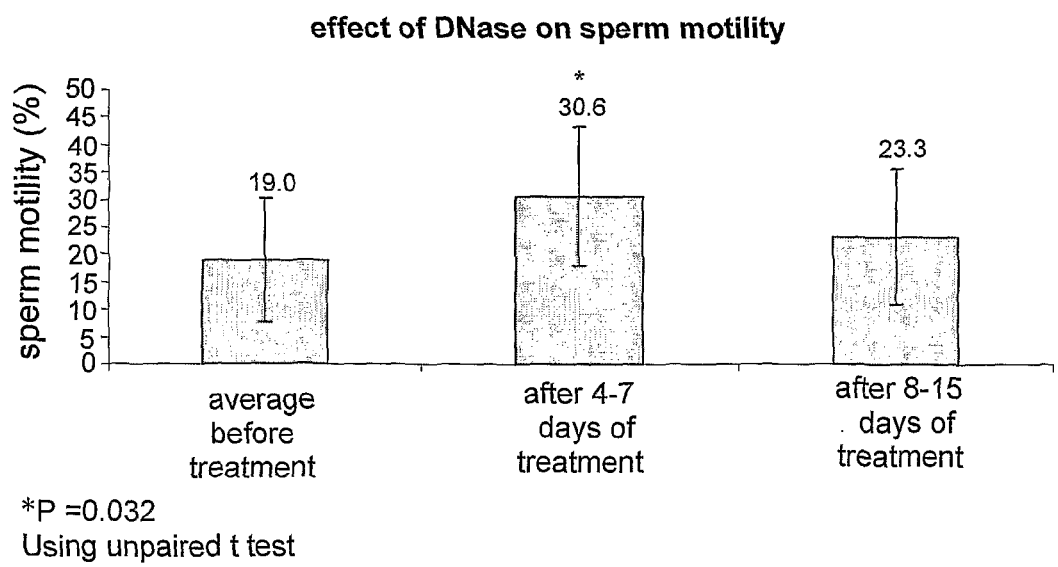
FIG. 12 is a histogram showing the effect of intramuscular DNase injections on sperm motility in semen of sub-fertile men.
Figure 13:
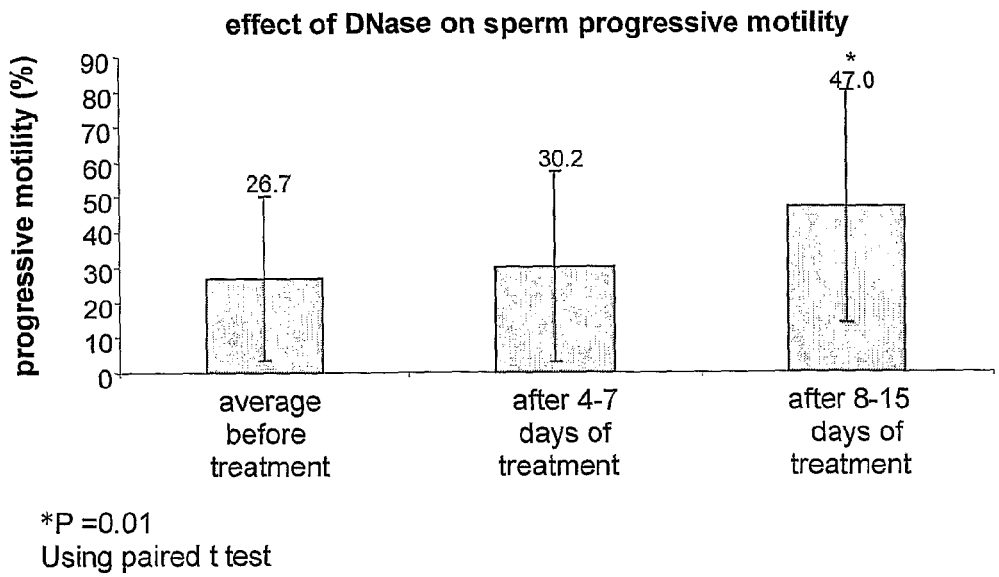
FIG. 13 is a histogram showing the effect of intramuscular DNase injections on sperm progressive motility in semen of sub-fertile men.

In order to examine whether DNase I can improve semen quality and fertility potential it was administered to sub-fertile men. In a group of 11 couples in which the male was previously identified as being sub-fertile and which failed to conceive in one IVF-ICSI treatment, the males received four times a day 25 mg of bovine DNase I by intramuscular (IM) injection for a period of 7-10 days. 7-11 days after the first injection the couples received a second ICSI treatment. Semen and blood samples were taken from the subjects twice before the beginning of the treatment and 4-7 and 8-15 days after the first injection and analyzed. As shown in FIG. 11, the semen analysis revealed that sperm density increased by 70% after 8-15 days of treatment compared to pre treatment ($24.28 \pm 14.73 \times 10^6$ cells/ejaculate vs. $14.31 \pm 10.15 \times 10^6$ cells/ejaculate respectively, $P<0.08$). In addition a 60% increase in sperm motility was observed after 4-7 days of treatment compared to pre treatment ($30.6 \pm 12.6\%$ vs. $19 \pm 11.3\%$ respectively, $P<0.033$, FIG. 12) and a 76% increase was observed in sperm progressive motility after 8-15 days of treatment compared to pre treatment ($47 \pm 33.1\%$ vs. $26.7 \pm 23.4\%$ respectively, $P<0.010$, FIG. 13).

Figure 14:
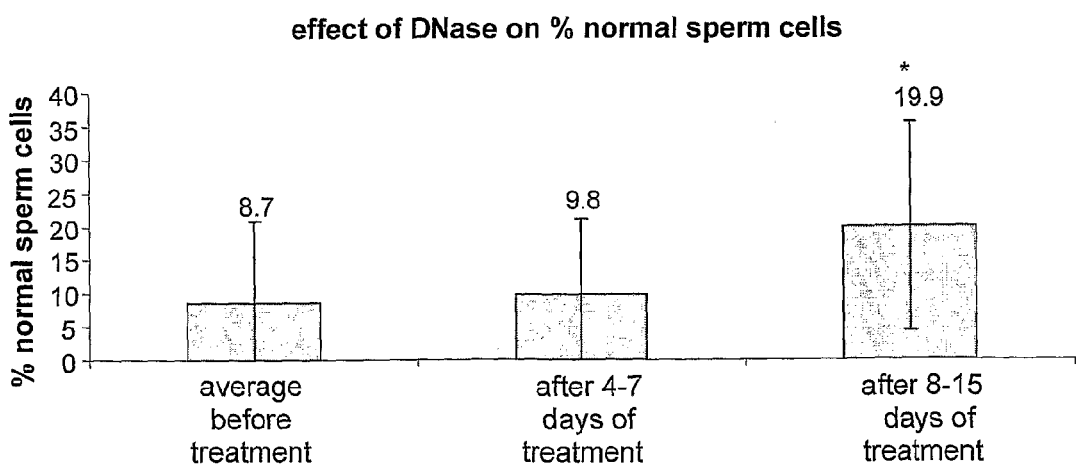
FIG. 14 is a histogram showing the effect of intramuscular DNase injections on the percentage of normal sperm cells in the semen of sub-fertile men as performed according to the WHO using light microscopy.
Figure 15:
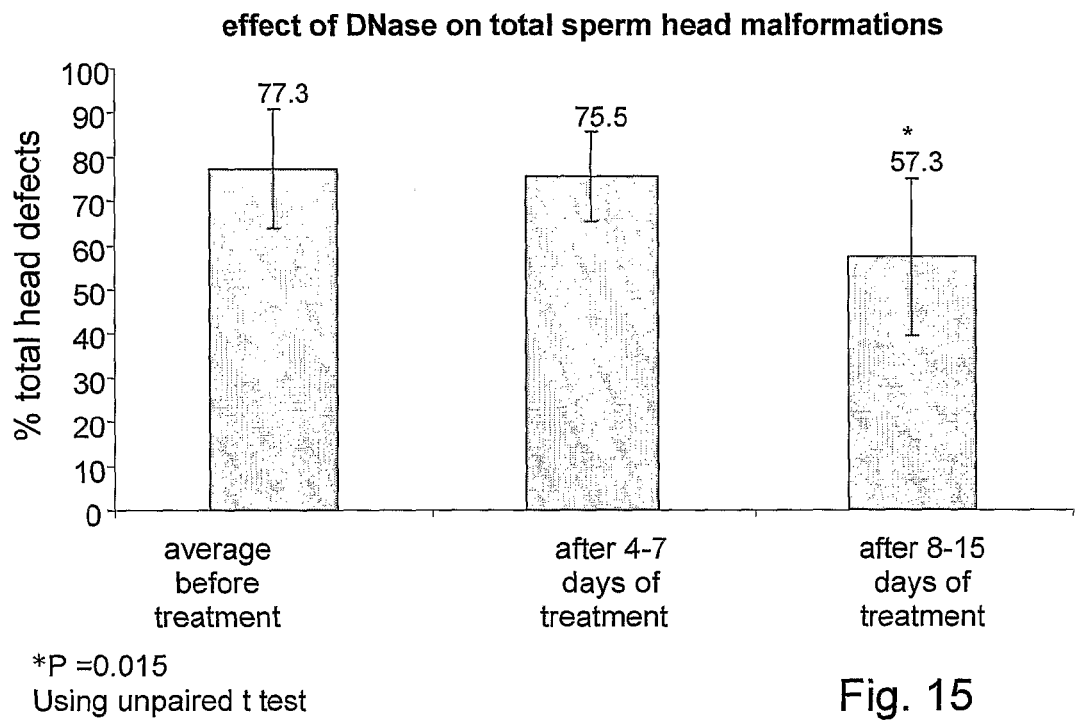
FIG. 15 is a histogram showing the effect of intramuscular DNase injections on the percentage of sperm cells with different head defects in the semen of sub-fertile men as performed according to the WHO using light microscopy.
Figure 16:
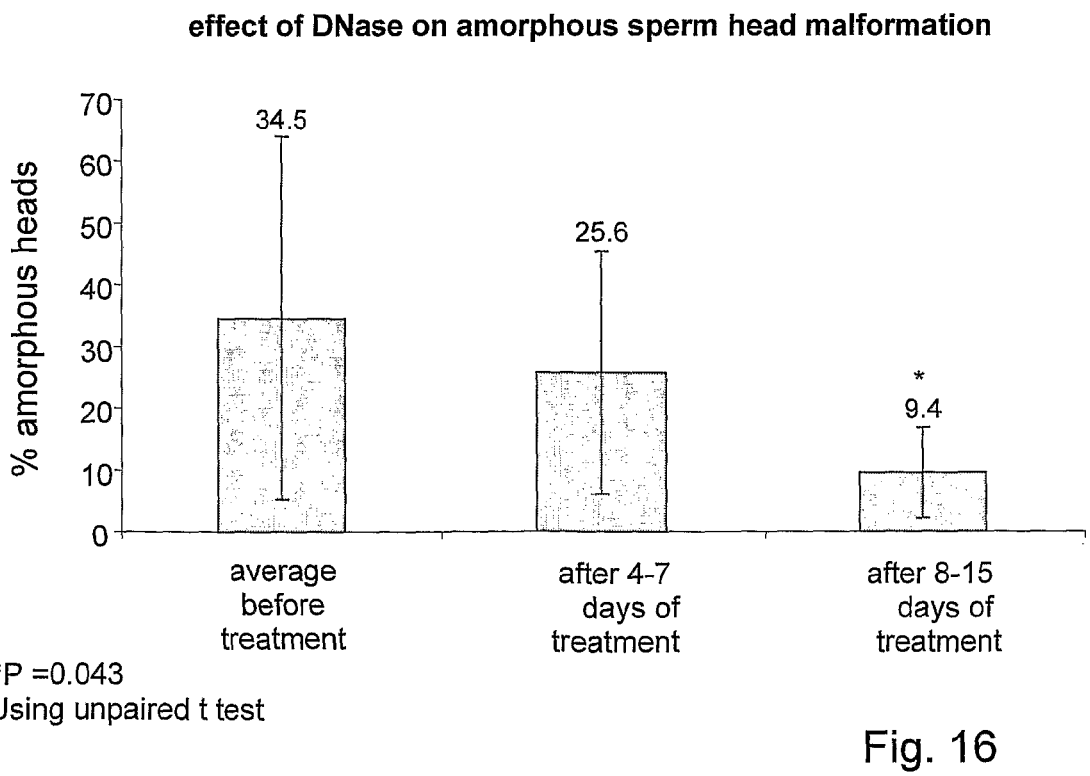
FIG. 16 is a histogram showing the effect of intramuscular DNase injections on the percentage of sperm cells with amorphous heads in the semen of sub-fertile men as performed according to the WHO using light microscopy.
Figure 17:
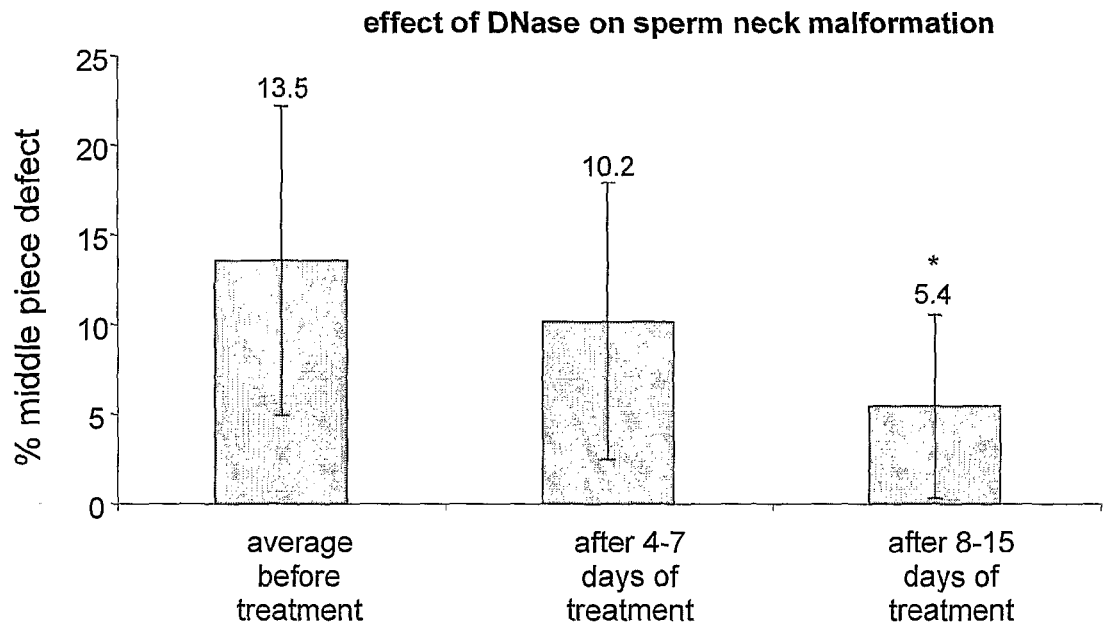
FIG. 17 is a histogram showing the effect of intramuscular DNase injections on the percentage of sperm cells with middle piece defects in the semen of sub-fertile men as performed according to the WHO using light microscopy.

The morphology of the sperm cells was analyzed according to the WHO guidelines (10). After 8-15 days of DNase treatment the percentage of morphologically shaped sperm cells in the semen of the subjects was elevated by 129% compared to pre-treatment ($19.9 \pm 12.1\%$ vs. $8.7 \pm 15.6\%$ respectively, $P<0.098$, FIG. 14). In addition it was shown that DNase treatment caused a 24% reduction in the percentage of total head defects after 8-15 days of treatment compared to pre treatment ($57.3 \pm 17.6\%$ vs. $77.3 \pm 13.4\%$ respectively, $P<0.015$, FIG. 15). In particular a 73% reduction was observed in the percentage of amorphous heads after 8-15 days of treatment compared to pre treatment ($9.4 \pm 7.3\%$ vs. $34.5 \pm 29.3\%$ respectively, $P<0.043$, FIG. 16). In addition a 60% reduction was observed in the percentage of middle piece defects after 8-15 days of treatment compared to pre treatment ($5.4 \pm 5.1\%$ vs. $13.5 \pm 8.6\%$ respectively, $P<0.040$, FIG. 17). The morphology of the sperm cells was analyzed also by MSOME in 3 subjects. An improvement in a variety of MSOME parameters was observed for these subjects after the DNase treatment (Table 1). In particular, there is an improvement in the percent of sperm cells with normal nucleus.

TABLE 1

|  | Subject No. 1 | | Subject No. 2 | | Subject No. 3 | | Average | |
| --- | --- | --- | --- | --- | --- | --- | --- | --- |
|  | | After 10 | | After 10 | | After 11 | | |
|  | Before treatment | days of treatment | Before treatment | days of treatment | Before treatment | days of treatment | Before treatment | After treatment |
| Sperm cells considered for MSOME analysis (%) | 90.7 | 94 | 95.3 | 98 | 83.4 | 90.7 | 89.8 | 94.2* |
| Sperm cells not considered for MSOME analysis (%) | 9.3 | 6 | 4.7 | 2 | 16.65 | 9.3 | 10.2 | 5.8* |
| Sperm cells with normal nucleus (suitable for IMSI selection, first and second choice) (%) | 4 | 7.3 | 1.3 | 5.4 | 1.6 | 2.7 | 2.3 | 5.1* |

*P < 0.093

Figure 18:
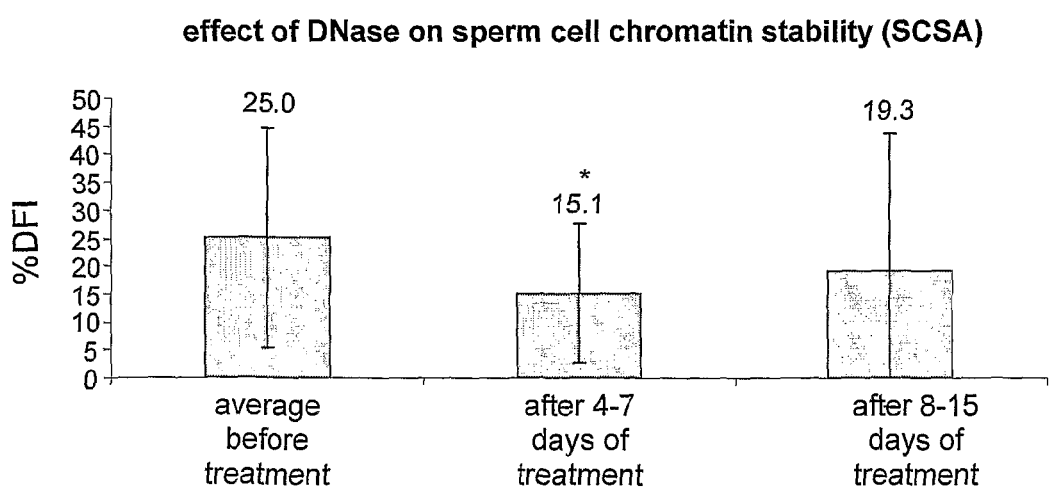
FIG. 18 is a histogram showing the effect of intramuscular DNase injections on sperm cell chromatin stability in the semen of sub-fertile men.
Figure 19:
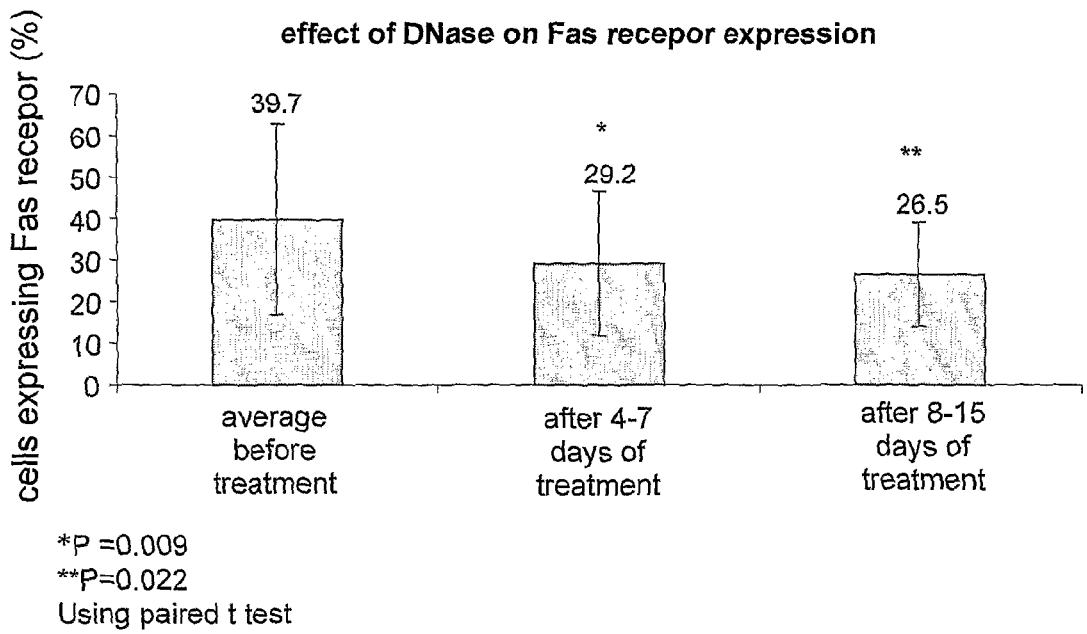
FIG. 19 is a histogram showing the effect of intramuscular DNase injections on the percentage of sperm cells expressing Fas receptor in the semen of sub-fertile men.

DNA damage in sperm cells is correlated with impaired conception rates as well as with the health of the offspring. One of the most employed methods to assess this damage is the "sperm chromatin structure assay" (SCSA), which measures the stability of sperm chromatin in cells exposed to acidic media. FIG. 18 shows that DNase treatment caused an elevation in sperm cell chromatin stability (smaller % DFI values) after 4-7 days of treatment compared to pre treatment (15.1±12.4% vs. 25±19.6% respectively, P<0.033). In addition DNase treatment caused a reduction in the expression of the apoptotic marker Fas receptor in sperm cell both after 4-7 and 8-15 days of treatment compared to pre treatment (26.5±12.5% and 29.2±17.4% vs. 39.7±23% respectively, P<0.009 for 4-7 days and P<0.023 for 8-15 days, FIG. 19).

Four out of the 11 couples (36%) become pregnant after the second ICSI treatment which followed the DNase treatment. The average pregnancy rate of a first ICSI cycle in the IVF center in which this trial was conducted is 25% [range 18%-32%]. The pregnancy rate of a second ICSI cycle of untreated patients in this IVF center is unknown since after one unsuccessful ICSI, they do not perform a second ICSI but rather advise the ICSI failures to use donor insemination. In any case, the 36% success rate of the second ICSI treatment is above the 25% of the IVF center, thus it is clear that DNase treatment improved the chances for pregnancy of ICSI treatments.

The results in FIGS. 11 to 19 and Table 1 show that intramuscular administration of DNase I improved the semen in most of the semen quality parameters. Sperm density was improved by 70% at the end of the experiment. Sperm motility improved by 60% already after 4-7 days of treatment but a reduction in motility occurred later possibly due to an immune response that took place around the seventh day and was observed as a 24 hour fever. Sperm progressive motility improved by 76% at the end of the experiment. The elevation in sperm motility and sperm density improved the fertility potential of the subjects and allowed those that could not succeed in the first ICSI treatment to conceive in a second ICSI treatment and possibly also in other ART treatments such as classical IVF or even an NI treatment.

Intramuscular DNase administration also improved sperm morphology as analyzed according to the WHO guidelines (10). The percentage of normal sperm cells was elevated by 129%. The percentage of sperm cells with head defects was reduced by 24% and brought to normal value (<65). The percentage of sperm cells with amorphous heads was reduced by 73% and the percentage of sperm cells with middle piece defects was reduced by 60%. An improvement in sperm morphology was observed also using MSOME. The number of sperm cells considered for MSOME analysis and the number of sperm cells with normal nucleus rose after treatment. The number of sperm cells with nuclear vacuoles, the number of narrow form sperm cells and the number of sperm cells with regional disorder was reduced.

In addition DNase treatment reduced damage in sperm cells. Sperm cell chromatin damage (as assessed by SCSA) was reduced by 40% already after 4-7 days of treatment and expression of the apoptotic marker Fas receptor was reduced by 26% after 4-7 days and by 33% after 8-15 days. The improvement in semen quality observed following DNase treatment is expected to improve fertility potential and indeed an increase in the success rate of ICSI treatment was observed after treatment.

Oral Administration of DNase I

Figure 20:
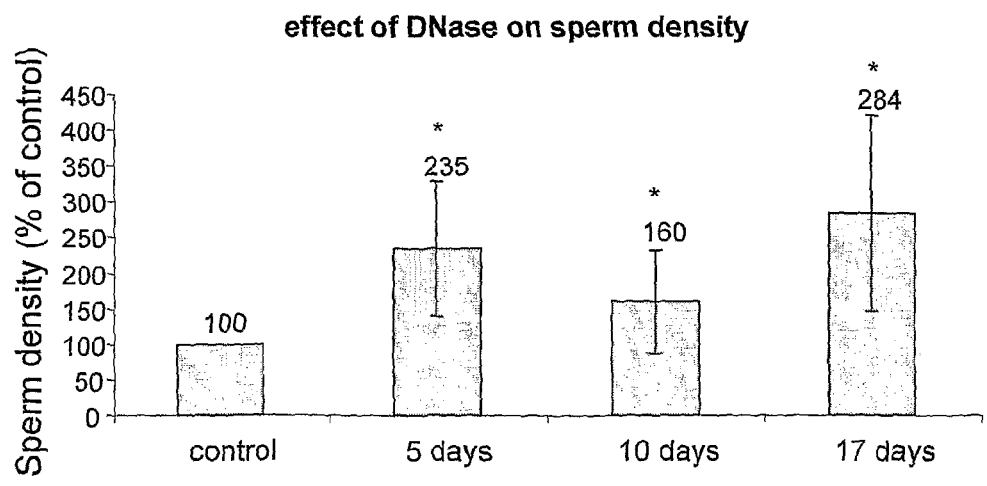
FIG. 20 is a histogram showing the effect of oral administration of DNase on sperm density.

In order to examine whether oral administration of DNase I can improve semen quality as observed with intramuscular administration, a group of 9 men received orally four times a day 50 mg of DNase I over a period of 16 days. Semen samples were taken and analyzed from the subjects 5 days before the onset of treatment, on the starting day of the treatment, and on days 5, 10 and 17 of the treatment. As can be seen in Table 2, the semen analysis revealed that sperm density (total spermatozoa/ejaculate) increased significantly post treatment compared to pre treatment (103±50×$10^6$ cells/ejaculate vs. 42±38×$10^6$ cells/ejaculate respectively, P<0.05). When results were expressed as % of control, an increase in sperm density was observed already after 5 days of treatment and more dramatically after 10 and 17 days of treatment (235±95%, 160±72% and 284±138% vs. 100% in control respectively, P<0.005, FIG. 20).

TABLE 2

| Routine Parameters | −5 | 0 | 5 | 10 | 17 |
|---|---|---|---|---|---|
| Volume (ml) | 1.2 ± 0.5 | 1.4 ± 0.6 | 1.8 ± 0.7 | 1.7 ± 0.8 | 2.3 ± 0.6** |
| Concentration (×$10^6$ cells/ml) | 31 ± 13 | 30 ± 12 | 42 ± 15 | 37 ± 12 | 45 ± 16* |
| Total spermatozoa (×$10^6$ cells/ej) | 37 ± 30 | 42 ± 38 | 75 ± 46 | 63 ± 52 | 103 ± 50* |
| % Sperm Motility | 85 ± 22 | 52 ± 5 | 61 ± 21 | 72 ± 12 | 86 ± 33 |
| % Sperm Viability | 76 ± 13 | 72 ± 11 | 71 ± 12 | 71 ± 12 | 77 ± 10 |
| % Normal forms | 15 ± 8 | 11 ± 5 | 17 ± 16 | 18 ± 10 | 15 ± 9 |
| % Head defects | 67 ± 10 | 70 ± 7 | 70 ± 16 | 72 ± 15 | 67 ± 9 |
| % Mead peace defects | 6 ± 3 | 8 ± 4 | 6 ± 4 | 7 ± 2 | 6 ± 3 |
| % Tail defects | 15 ± 10 | 12 ± 12 | 8 ± 6 | 12 ± 8 | 12 ± 6 |

*p < 0.05, n = 9
**p < 0.001, n = 9

Figure 21:
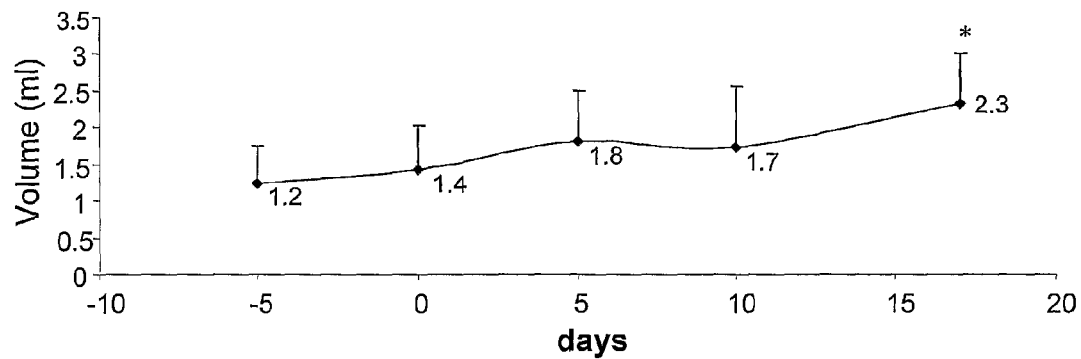
FIG. 21 is a graph showing the effect of oral administration of DNase on semen volume.
Figure 22:
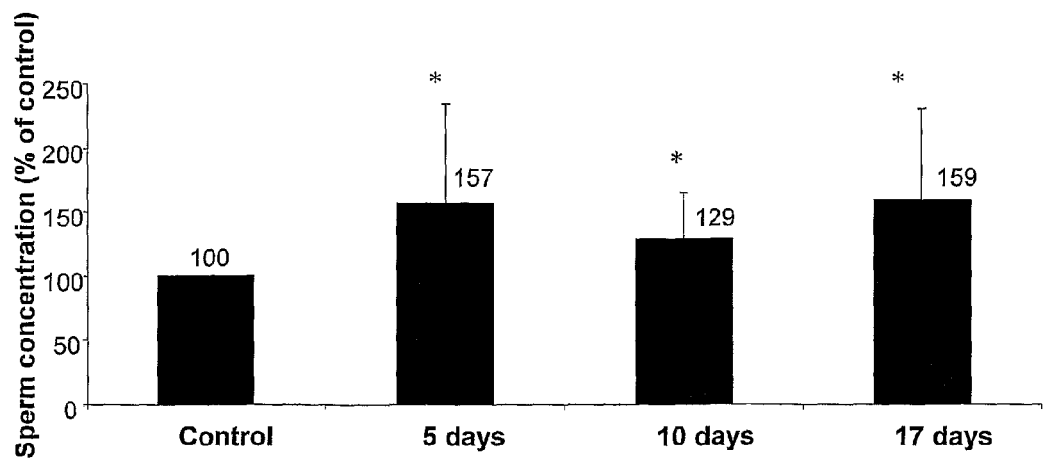
FIG. 22 is a histogram showing the effect of oral administration of DNase on sperm cell concentration.

In addition, an increase in semen volume was observed after 17 days of treatment (1.3±0.5 ml pre treatment vs. 2.3±0.6 ml after 17 days of treatment, P<0.001, Table 2 and FIG. 21). This increase indicates an augmented function of the accessory glands. As shown in Table 2 and in FIG. 22, the sperm concentration also increased during the treatment.

Figure 23:
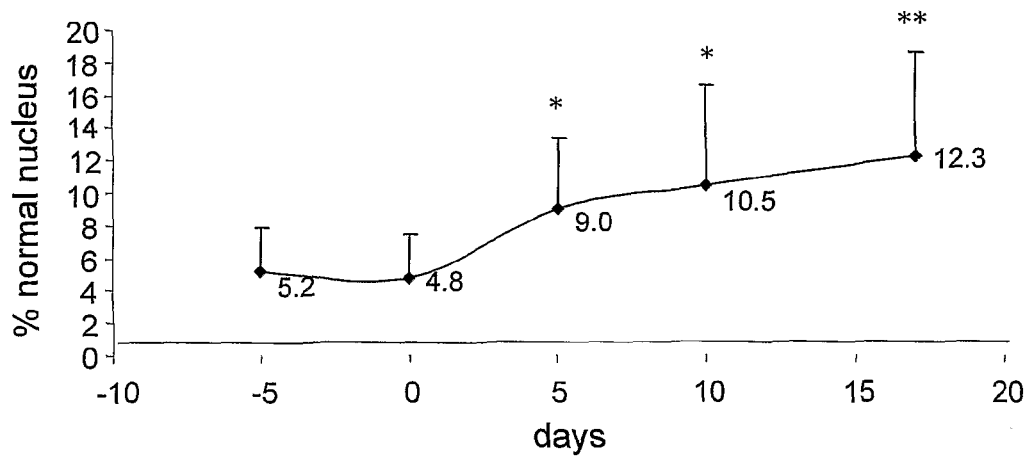
FIG. 23 is a graph showing the effect of oral administration of DNase on the percentage of sperm cells with normal nucleus morphology performed by MSOME.
Figure 24:
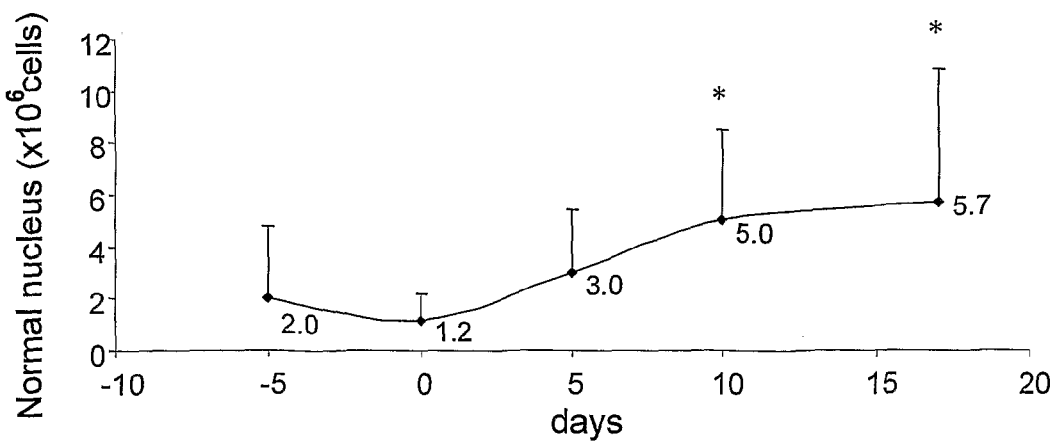
FIG. 24 is a graph showing the effect of oral administration of DNase on the number of sperm cells with normal nucleus morphology performed by MSOME.
Figure 25:
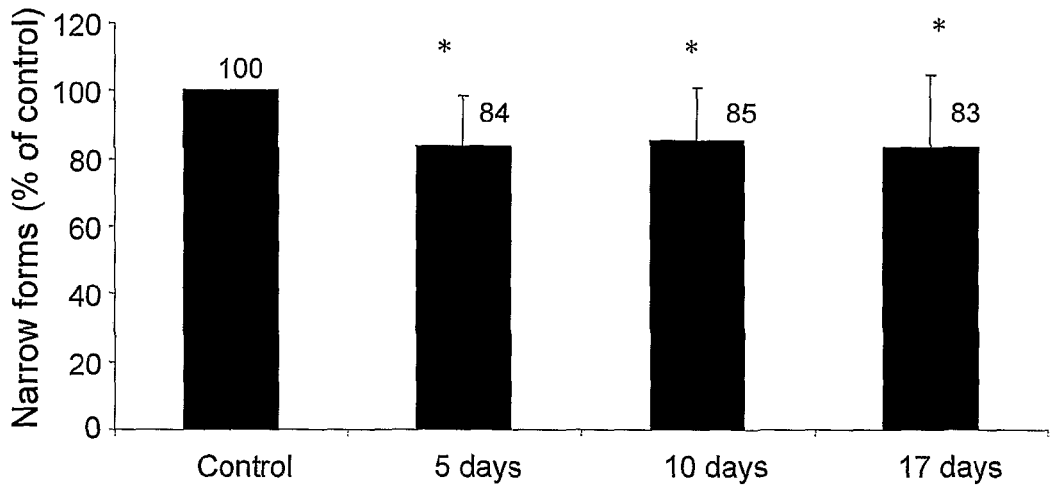
FIG. 25 is a histogram showing the effect of oral administration of DNase on the percentage of sperm cells with narrow head morphology as performed by MSOME.

MSOME analysis showed that the percentage of sperm cells having a normal nucleus increased 2 fold already after 5 and 10 days of treatment compared to pre treatment levels, as showed in Table 3 and FIG. 23. There was also an increase in the number of sperm cells with normal nucleus after 10 and 17 days of treatment compared to pre treatment (5.0±3.4×$10^6$ cells and 5.7±5.1×$10^6$ cells vs. 1.6±2.1×$10^6$ cells respectively, P<0.05, Table 3 and FIG. 24). In addition a decrease in sperm cells with narrow heads was observed after 5, 10 and 17 day of treatment compared to control (84±15%, 85±15% and 83±21% vs. 100% in control, respectively, P<0.05, FIG. 25).

TABLE 3

| MSOME Parameters | −5 | 0 | 5 | 10 | 17 |
|---|---|---|---|---|---|
| % Normal nucleus | 5.2 ± 2.7 | 4.7 ± 2.6 | 9.0 ± 4.3* | 10.4 ± 6.1* | 12.3 ± 6.3** |
| Normal nucleus (×$10^6$ cells) | 2.0 ± 2.7 | 1.2 ± 0.9 | 3.0 ± 2.4 | 5.0 ± 3.4* | 5.7 ± 5.1* |
| Total abnormal forms | 159 ± 31 | 154 ± 30 | 154 ± 30 | 150 ± 28 | 151 ± 30 |
| % Nuclear Vacuoles | 80 ± 13 | 79 ± 14 | 79 ± 12 | 73 ± 13 | 77 ± 10 |
| % Small forms | 0.1 ± 0.3 | 0.5 ± 0.8 | 0.4 ± 1.2 | 0.1 ± 0.3 | 0.4 ± 0.6 |
| % Large forms | 3.3 ± 2.3 | 4.4 ± 2.3 | 3.9 ± 2.1 | 2.2 ± 1.4 | 2.5 ± 2.3 |
| % Narrow forms | 40 ± 10 | 41 ± 14 | 33 ± 10 | 35 ± 9 | 34 ± 9 |
| % Wide forms | 4.2 ± 3.0 | 3.2 ± 2.4 | 3.5 ± 2.0 | 5.2 ± 4.0 | 2.9 ± 2.0 |
| % Regional disorder | 31 ± 7 | 26 ± 11 | 34 ± 8 | 34 ± 9 | 34 ± 8 |
| Vacuole Index | 1.8 ± 0.3 | 1.8 ± 0.3 | 1.7 ± 0.2 | 1.6 ± 0.3 | 1.7 ± 0.3 |

*p < 0.05, n = 9
**p < 0.001, n = 9

Figure 26:
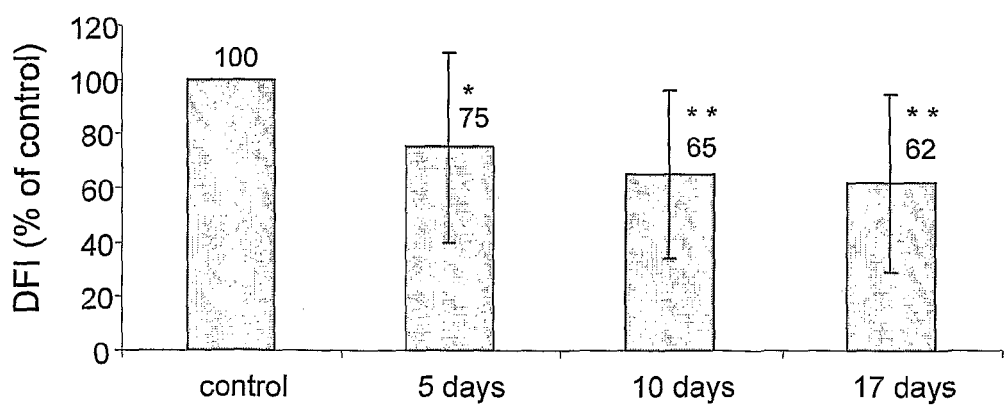
FIG. 26 is a histogram showing the effect of oral administration of DNase on sperm cell chromatin stability.
Figure 27:
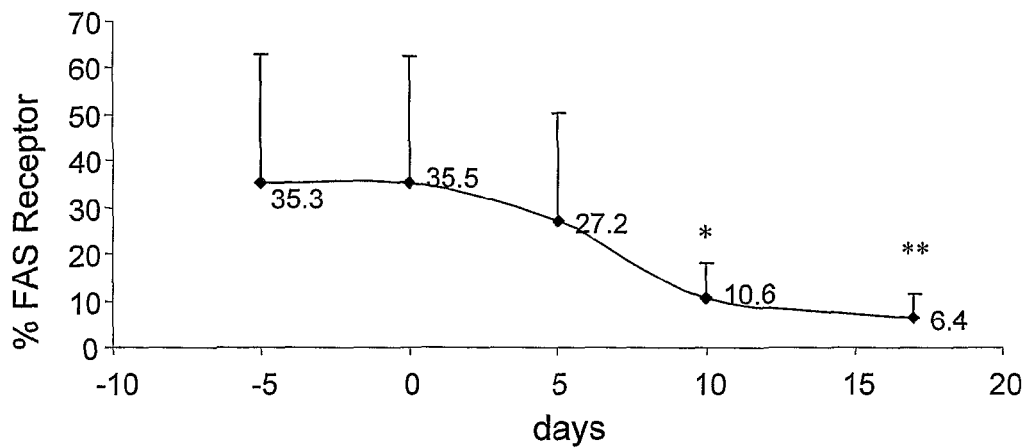
FIG. 27 is a graph showing the effect of oral administration of DNase on the percentage of sperm cells expressing Fas receptor.

An increase in sperm cell chromatin stability (smaller DFI values) was observed already after 5 days of treatment compared to control (75±35% vs. 100% respectively, P<0.05, FIG. 26). This decreased was more pronounced after 10 and 17 days (65±31% and 62±33% vs. 100% respectively, P<0.005, FIG. 26). In addition the percentage of sperm cells expressing the apoptotic marker Fas receptor decreased after 10 days of treatment compared to pre treatment (10.6±7.5% vs. 35.4±26.4% respectively, P<0.05, FIG. 27). A further decrease was observed after 17 days of treatment compared to pre treatment (6.4±5.2% vs. 35.4±26.4%, respectively, P<0.005, FIG. 27).

Among the subjects that participated in the orally administered DNase experiment, only one subject attempted with his female partner to achieve pregnancy. This couple had previously failed in four IUI procedures. Following the DNase treatment the couple achieved spontaneous pregnancy.

The results in FIGS. 20 to 27 and Tables 2 and 3 show that oral administration of DNase I has the following effects:

1. Increasing semen volume.
2. Increasing sperm cell concentration and density.
3. Improving spermatozoa quality by increasing the fraction of sperm cells having a normal nucleus, increasing chromatin stability and decreasing the proportion of Fas receptor expressing cells.

Figure 28:
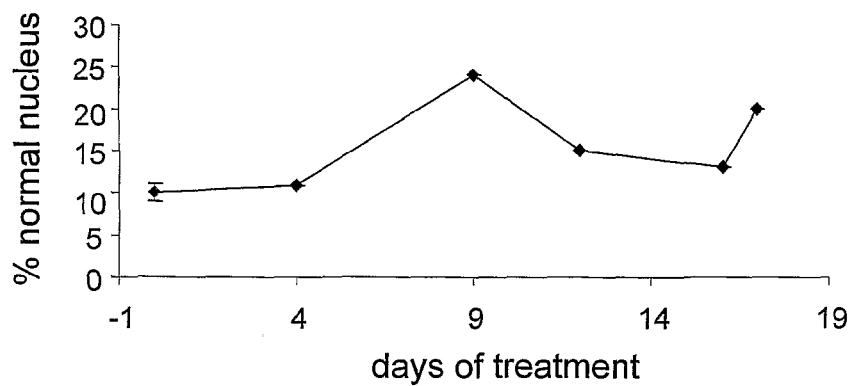
FIG. 28 is a graph showing the effect of DNase inhalation on the percentage of sperm cells with normal nucleus morphology performed by MSOME.

In order to examine whether administration of DNase by inhalation leads to similar affects on semen quality, it was examined for one case. At the inhalation procedure the subject inhaled three times a day 8 mg of the enzyme, taken in 4 hours intervals. Inhalation of the enzyme led to elevation in the percentage of normal nuclei that was most profound after 9 and 17 days of inhalation (FIG. 28).

Inhibition of Endogenous Sperm Cell DNase

Figure 29:
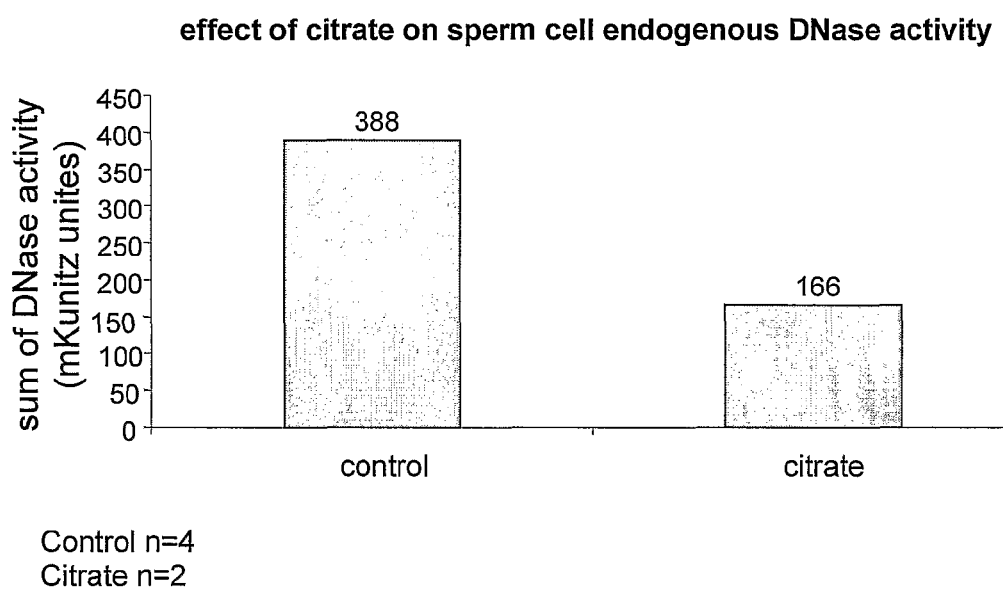
FIG. 29 is a histogram showing the inhibition of internal sperm cell DNase activity by the DNase inhibitor citrate.

In order to examine whether the DNase inhibitor citrate can inhibit intracellular sperm cell DNase, sperm cells were incubated with or without 10 mM citrate for up to 8 hours. The intracellular DNase activity was measured every hour and the sum of the DNase activity was calculated. The sum of the DNase activity in the citrate treated sperm cells was 43% of that of control sperm cells (FIG. 29), indicating inhibition of intracellular DNase activity by citrate.

Figure 30:
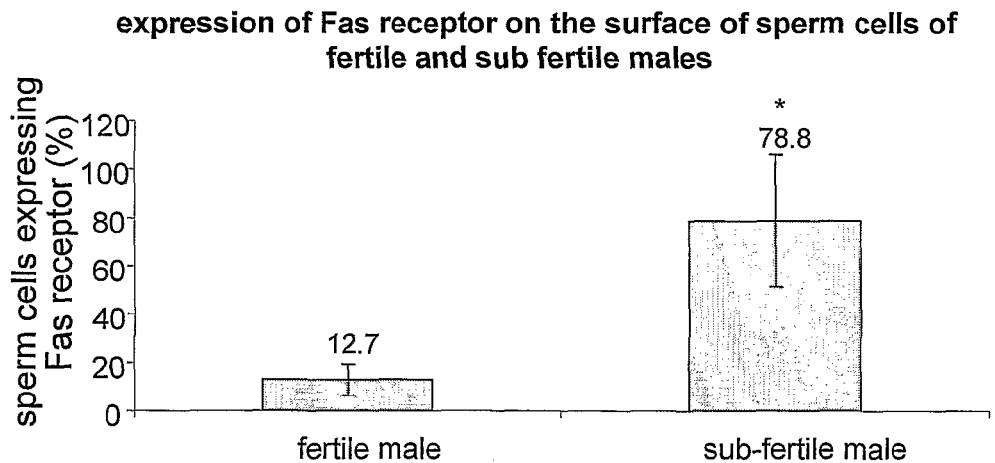
FIG. 30 is a histogram showing expression of Fas receptor on the surface of sperm cells of fertile and sub fertile men.
Figure 31:
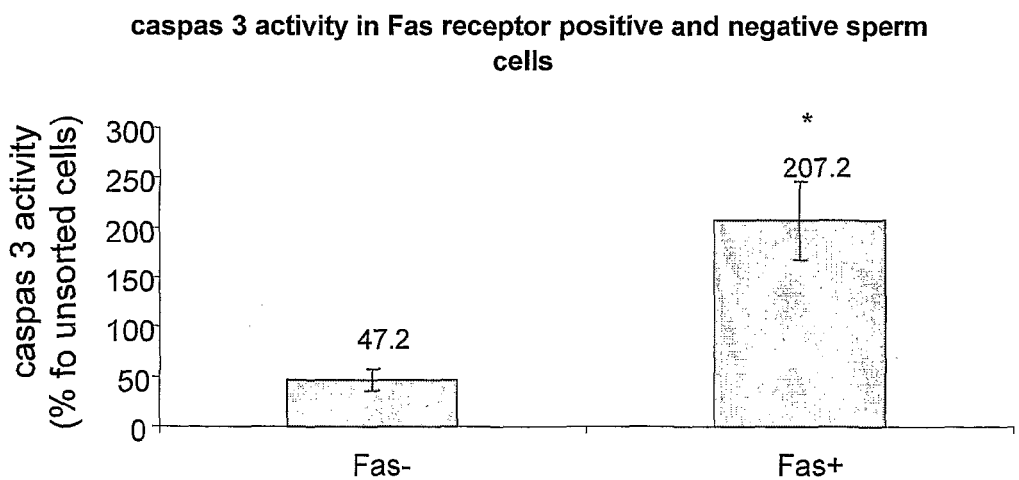
FIG. 31 is a histogram showing activity of caspas-3 in either Fas receptor expressing sperm cells or non-Fas receptor expressing sperm cells of sub-fertile men.

The Relationship Between Fas Receptor Expression and Caspas 3 Activity in Sperm Cells and Fertility One of the known markers of apoptosis is the expression of the Fas receptor. As observed in FIG. 4, injection of cell free DNA to mice leads to a statistically significant elevation in Fas receptor expression on the membrane of their sperm cells. In vitro incubation of sperm cells with cell free DNA leads as well to significant elevation in Fas receptor expression on sperm cells membrane (not shown). In order to determine whether there is a correlation between Fas receptor expression and male fertility, Fas receptor expression on the surface of sperm cells was determined in fertile and sub-fertile men. The percentage of Fas receptor expressing sperm cells was four fold higher in sub-fertile males than in fertile males (78.8±27.4 vs. 12.7±6.4, P<0.001, FIG. 30). Next in order to examine whether there is a correlation between Fas receptor expression in sperm cells of sub-fertile males and the activity of the apoptotic marker caspase-3, sperm cells from sub-fertile men were separated according to their expression of Fas receptor. Caspase-3 activity was determined in each sperm cell population. The percentage of caspase-3 activity in the Fas receptor positive sperm cells was 4-fold higher than caspase-3 activity in the Fas receptor negative subpopulation (207.2±39.6 vs. 47.2±10.5, P<0.001, FIG. 31).

Figure 32:
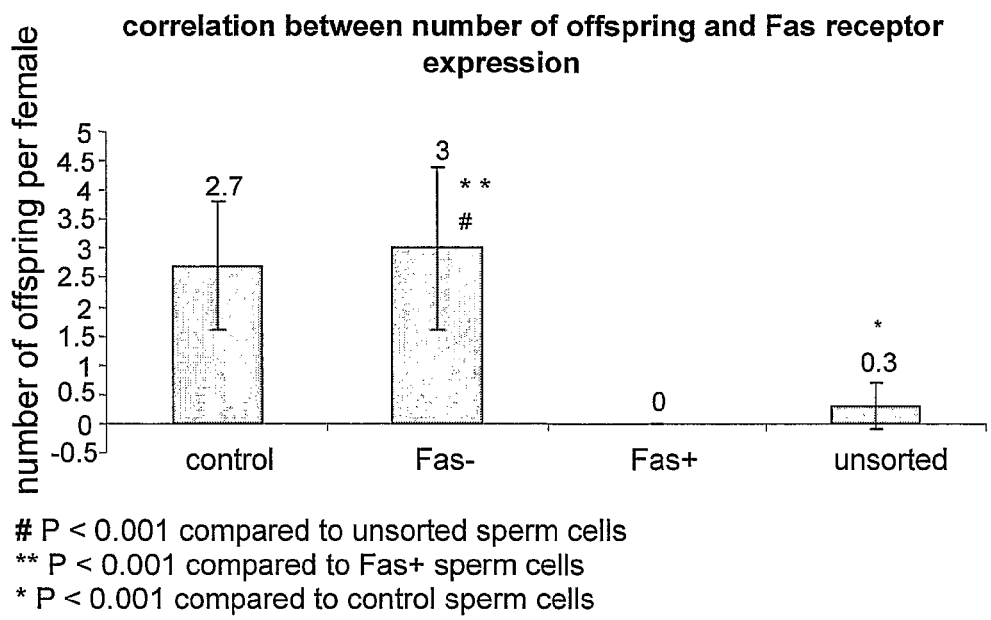
FIG. 32 is a histogram showing the number of offspring obtained in artificial insemination of mice using either Fas receptor expressing sperm cells or non-Fas receptor expressing sperm cells.

In order to determine whether Fas receptor expression is correlated with fertility potential, the following experiment was conducted: Mice sperm cells were incubated with cell free DNA (which was found to stimulate Fas receptor expression) and then Fas receptor expressing sperm cells were separated from non-Fas receptor expressing cells. Four groups of 10 female mice were inseminated with either sperm cells that express Fas receptor (Fas+), sperm cells that do not express Fas receptor (Fas−), sperm cells that were incubated with cell free DNA but not sorted according to Fas receptor expression, and control cells that were not exposed to DNA. All inseminations were performed with the same number of sperm cells. As can be seen in FIG. 32, no fetuses were obtained from insemination with Fas(+) sperm cells in contrast to insemination with Fas(−) sperm cells or control sperm cells that produced 3±1.4 and 2.7±1.1 average fetuses per female mouse, respectively. Insemination with cells that were incubated with cell free DNA but not sorted gave rise to only 0.3±0.4 average fetuses per female.

Figure 33:
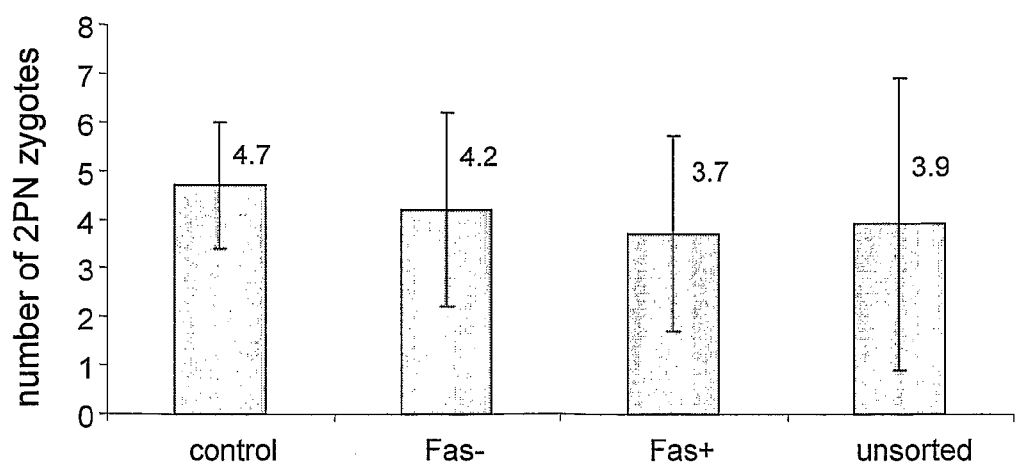
FIG. 33 is a histogram showing the number of 2PN zygotes obtained in artificial insemination of mice using either Fas receptor expressing sperm cells or non-Fas receptor expressing sperm cells.
Figure 34:
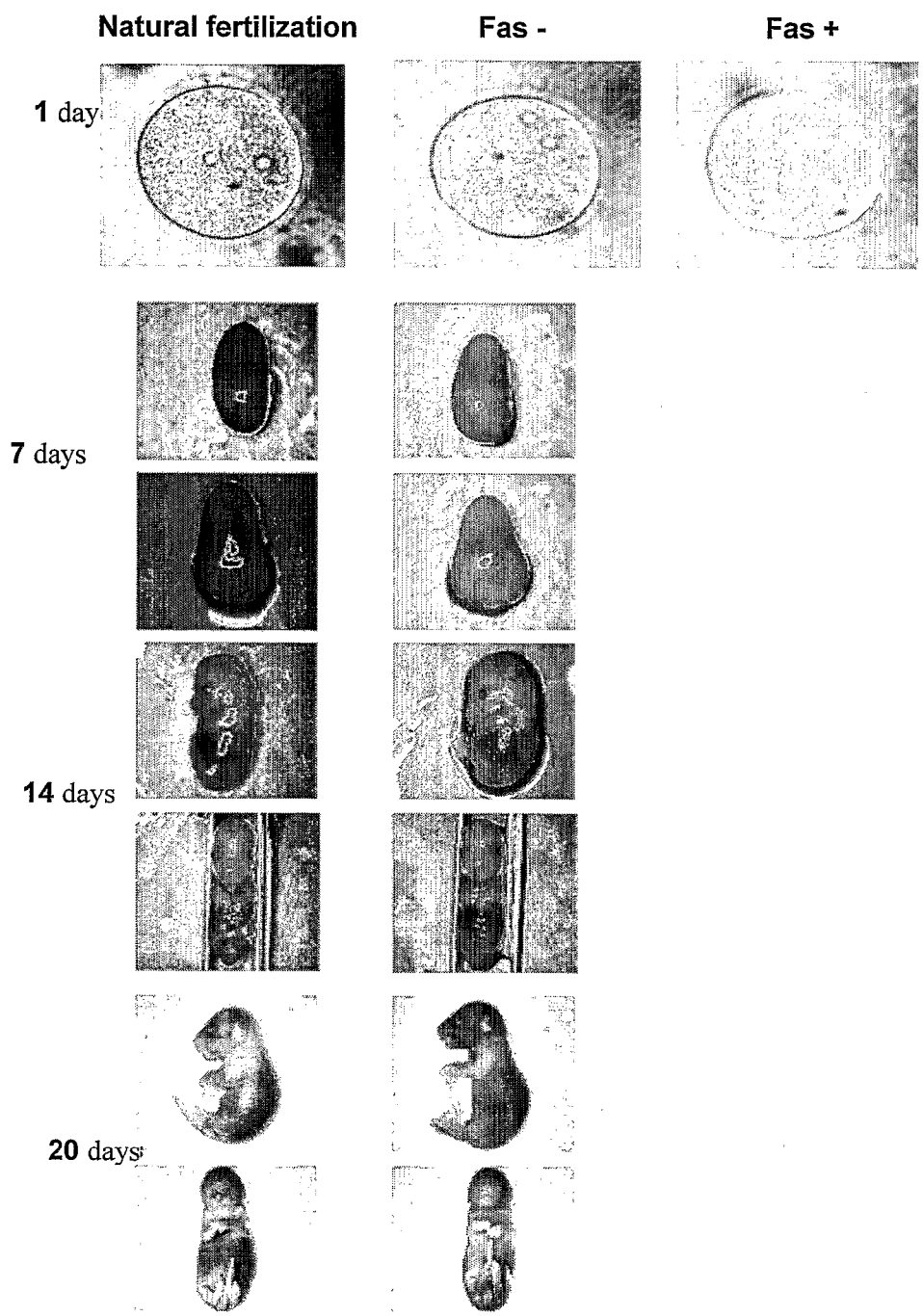
FIG. 34 shows embryonic development in mice following natural fertilization or following artificial insemination using either Fas receptor expressing sperm cells or non-Fas receptor expressing sperm cells.

In order to determine the stage in which Fas receptor expressing sperm cells fail to produce offspring, four groups of female mice were inseminated with sperm cells as described above. 16-20 hours after insemination, the females were sacrificed, oocytes were taken from the oviduct and the number of 2 pro nuclei (2PN) zygotes was counted. As shown in FIG. 33, the Fas(+) and the Fas(−) sperm cells gave rise to a similar number of 2PN zygotes and no significant difference was observed between control sperm cells and sperm cells which were incubated with cell free DNA. Then a similar insemination was performed using Fas(+) and Fas(−) sperm cells and the female mice were sacrificed at different stages of the pregnancy. Embryonic development was examined in both treatments and compared to embryonic development in natural fertilization. No embryonic development past the 2PN stage was observed in females inseminated with Fas(+) sperm cells while females inseminated with Fas(−) sperm cells exhibited normal embryonic development as in natural fertilization (FIG. 34).

Figure 35:
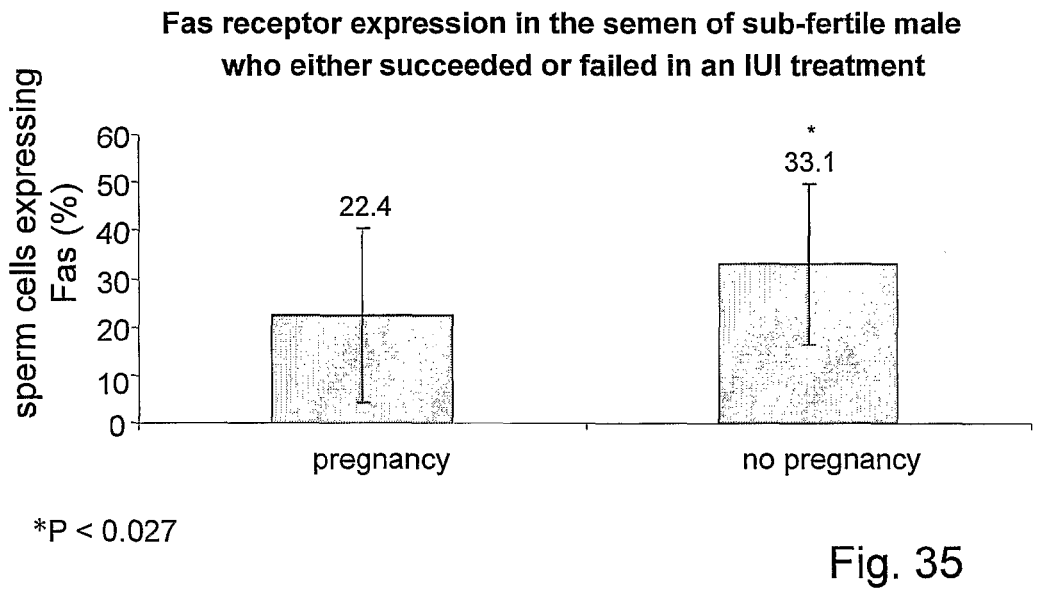
FIG. 35 is a histogram showing the percentage of sperm cells expressing Fas receptor in the semen of sub-fertile men that either succeeded or failed in an IUI treatment.

In addition the correlation between Fas receptor expression on sperm cells and IUI treatment outcome was examined in humans. Semen samples from 72 sub-fertile couples that underwent IUI treatment were examined for Fas expression by immunofluorescence staining with human anti Fas receptor and FACS analysis. 18 cases resulted in a pregnancy while the remaining 54 cases did not result in pregnancy. As shown in FIG. 35, the frequency of Fas(+) sperm cells in the group that achieved pregnancy was statistically lower than at the group that did not achieved pregnancy (22.4%±18.2 vs. 33.1%±16.6 respectively, P<0.027).

DNase Activity in Mouse Blood Plasma

Figure 36:
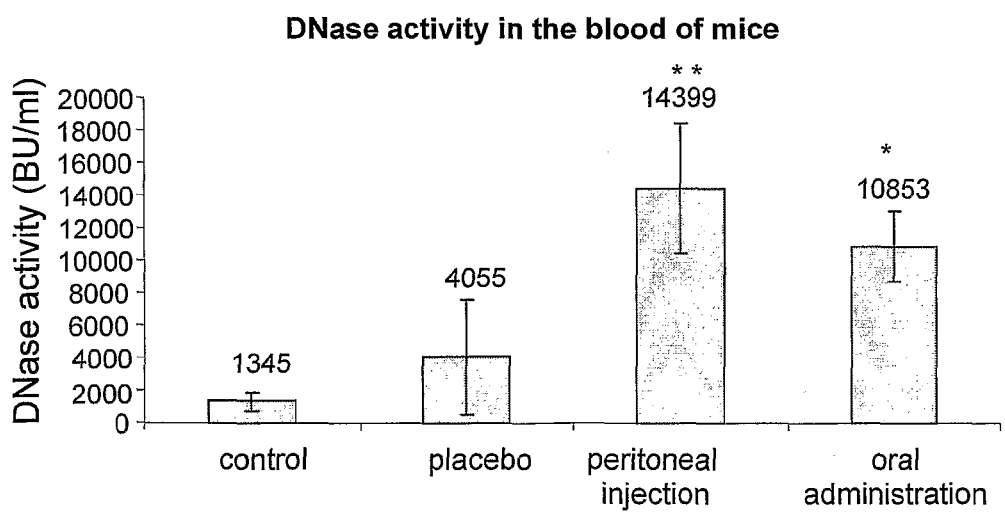
FIG. 36 is a histogram showing DNase activity in mouse blood plasma following administration of DNase.

In order to examine the ability of DNase to reach the blood stream upon oral administration, mice were treated with DNase either by intra peritoneal injection or oral administration and DNase activity was examined after 1 hour. As shown in FIG. 36, a significant increase in blood plasma DNase activity was observed both in the peritoneal injected and the oral administered groups in comparison to the negative control group (14399±4000 and 10853±2150, respectively, vs. 1345±580, p<0.001). A small elevation in DNase activity was also observed in the group that received placebo (4055±3500).

Animal Study Examining Safety and Efficacy of DNase

An animal study examining the safety and efficacy of DNase in rodents and dogs was performed at the Federal Institute of Toxicology in Russia. The study showed that acute and prolonged administration of DNase does not have a toxic effect on the warm-blooded laboratory animals studied. The prolonged (30 days) daily DNase administration to the experimental animals in doses that were over 100 times higher than the recommended dose for humans did not produce detectable harmful effects on the main body systems (nervous, cardiovascular, hemopoietic, secretory, respiratory), metabolism, general health condition, development and basic homeostatic parameters of the organism. The absence of irritating effects on the digestive system upon DNase administration was also observed.

The invention claimed is:

1. A method for treating male sub-fertility in an individual with elevated endogenous cell free DNA levels, comprising:
   administering systemically to the individual in need thereof, a therapeutically effective amount of a pharmaceutical composition, comprising
      an active ingredient being a deoxyribonuclease (DNase), and
      a physiologically acceptable carrier,
      wherein the pharmaceutical composition is administered for a duration of between about 7 days and about 74 days, and wherein after administration human cell free DNA levels are reduced and sub-fertility in the individual is ameliorated.

2. The method of claim 1, wherein the DNase is DNase I.

3. The method according to claim 1, wherein the DNase is of animal, plant, bacterial, viral, yeast, or protozoan origin or is a recombinant enzyme or a human recombinant DNase.

4. The method according to claim 1, in a dosage form suitable for oral administration.

5. The method according to claim 1, in a dosage form suitable for administration by inhalation.

6. The method according to claim 1, in a dosage form suitable for administration by injection.

7. The method according to claim 1, wherein the duration of the administration is acute, semi-chronic, or chronic.

8. The method according to claim 1, wherein administering systemically is by oral administration, intramuscular injection, subcutaneously injection, intravenous injection, or inhalation.

* * * * *